(12) United States Patent
Nakai

(10) Patent No.: US 11,752,287 B2
(45) Date of Patent: Sep. 12, 2023

(54) SYSTEMS AND METHODS FOR AUTOMATIC CYCLING OR CYCLING DETECTION

(71) Applicant: Covidien LP, Mansfield, MA (US)

(72) Inventor: Richard Nakai, Long Beach, CA (US)

(73) Assignee: Covidien LP, Mansfield, MA (US)

( * ) Notice: Subject to any disclaimer, the term of this patent is extended or adjusted under 35 U.S.C. 154(b) by 898 days.

(21) Appl. No.: 16/590,530

(22) Filed: Oct. 2, 2019

(65) Prior Publication Data

US 2020/0108215 A1    Apr. 9, 2020

Related U.S. Application Data

(60) Provisional application No. 62/740,740, filed on Oct. 3, 2018.

(51) Int. Cl.
*A61M 16/00* (2006.01)
*A61M 16/08* (2006.01)

(52) U.S. Cl.
CPC ...... *A61M 16/026* (2017.08); *A61M 16/0883* (2014.02); *A61M 2205/3303* (2013.01); *A61M 2205/502* (2013.01); *A61M 2230/40* (2013.01); *A61M 2230/60* (2013.01)

(58) Field of Classification Search
CPC ............ A61M 16/026; A61M 16/0883; A61M 16/024; A61M 16/0063; A61M 2205/3303; A61M 2205/502; A61M 2205/505; A61M 2230/40; A61M 2230/60; A61M 2230/46; A61B 5/085; A61B 5/087; A61B 5/4836
See application file for complete search history.

(56) References Cited

U.S. PATENT DOCUMENTS

| | | |
|---|---|---|
| 3,575,167 A | 4/1971 | Michielsen |
| 3,677,267 A | 7/1972 | Richards |
| 3,908,704 A | 9/1975 | Clement et al. |
| 4,095,592 A | 6/1978 | Delphia |
| 4,401,116 A | 8/1983 | Fry et al. |
| 4,421,113 A | 12/1983 | Gedeon et al. |
| 4,444,201 A | 4/1984 | Itoh |
| 4,702,240 A | 10/1987 | Chaoui |
| 4,721,060 A | 1/1988 | Cannon et al. |
| 4,790,832 A | 12/1988 | Lopez |
| 4,870,961 A | 10/1989 | Barnard |
| 5,016,626 A | 5/1991 | Jones |

(Continued)

FOREIGN PATENT DOCUMENTS

| | | |
|---|---|---|
| EP | 521515 | 1/1993 |
| EP | 1005829 | 6/2000 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Justine R Yu
*Assistant Examiner* — Kelsey E Baller

(57) ABSTRACT

Systems and methods for novel ventilation that allows the ventilator to detect a patient intention to cycle exhalation are provided. Further, systems and methods for cycling exhalation based on a muscle pressure are provided.

20 Claims, 8 Drawing Sheets

(56) References Cited

U.S. PATENT DOCUMENTS

| | | |
|---|---|---|
| 5,074,297 A | 12/1991 | Venegas |
| 5,080,093 A | 1/1992 | Raabe et al. |
| 5,086,767 A | 2/1992 | Legal |
| 5,117,818 A | 6/1992 | Palfy |
| 5,127,398 A | 7/1992 | Stone |
| 5,129,390 A | 7/1992 | Chopin et al. |
| 5,134,994 A | 8/1992 | Say |
| 5,148,802 A | 9/1992 | Sanders et al. |
| 5,165,398 A | 11/1992 | Bird |
| 5,174,284 A | 12/1992 | Jackson |
| 5,195,512 A | 3/1993 | Rosso |
| 5,211,170 A | 5/1993 | Press |
| 5,235,973 A | 8/1993 | Levinson |
| 5,239,995 A | 8/1993 | Estes et al. |
| 5,259,374 A | 11/1993 | Miller et al. |
| 5,273,032 A | 12/1993 | Borody |
| 5,279,549 A | 1/1994 | Ranford |
| 5,303,698 A | 4/1994 | Tobia et al. |
| 5,303,700 A | 4/1994 | Weismann et al. |
| 5,307,794 A | 5/1994 | Rauterkus et al. |
| 5,316,009 A | 5/1994 | Yamada |
| 5,318,017 A | 6/1994 | Ellison |
| 5,320,093 A | 6/1994 | Raemer |
| 5,322,057 A | 6/1994 | Raabe et al. |
| 5,323,772 A | 6/1994 | Linden et al. |
| 5,335,650 A | 8/1994 | Shaffer et al. |
| 5,373,842 A | 12/1994 | Olsson et al. |
| 5,383,448 A | 1/1995 | Tkatchouk et al. |
| 5,385,142 A | 1/1995 | Brady et al. |
| 5,395,301 A | 3/1995 | Russek |
| 5,398,676 A | 3/1995 | Press et al. |
| 5,398,682 A | 3/1995 | Lynn |
| 5,419,314 A | 5/1995 | Christopher |
| 5,429,123 A | 7/1995 | Shaffer et al. |
| 5,429,124 A | 7/1995 | Yoshida et al. |
| 5,433,193 A | 7/1995 | Sanders et al. |
| 5,435,305 A | 7/1995 | Rankin, Sr. |
| 5,471,977 A | 12/1995 | Olsson et al. |
| 5,474,062 A | 12/1995 | DeVires et al. |
| 5,494,028 A | 2/1996 | DeVries et al. |
| 5,513,631 A | 5/1996 | McWilliams |
| 5,537,999 A | 7/1996 | Dearman et al. |
| 5,540,220 A | 7/1996 | Gropper et al. |
| 5,542,415 A | 8/1996 | Brody |
| 5,542,416 A | 8/1996 | Chalvignac |
| 5,551,418 A | 9/1996 | Estes et al. |
| 5,558,086 A | 9/1996 | Smith et al. |
| 5,562,918 A | 10/1996 | Stimpson |
| 5,564,416 A | 10/1996 | Jones |
| 5,582,163 A | 12/1996 | Bonassa |
| 5,590,651 A | 1/1997 | Shaffer et al. |
| 5,596,983 A | 1/1997 | Zander et al. |
| 5,603,316 A | 2/1997 | Coufal et al. |
| 5,606,968 A | 3/1997 | Mang |
| 5,632,269 A | 5/1997 | Zdrojkowski |
| 5,642,726 A | 7/1997 | Owens et al. |
| 5,647,351 A | 7/1997 | Weismann et al. |
| 5,651,361 A | 7/1997 | Dearman et al. |
| 5,655,519 A | 8/1997 | Alfery |
| 5,669,379 A | 9/1997 | Somerson et al. |
| 5,687,713 A | 11/1997 | Bahr et al. |
| 5,692,497 A | 12/1997 | Schnitzer et al. |
| 5,724,962 A | 3/1998 | Vidgren et al. |
| 5,735,267 A | 4/1998 | Tobia |
| 5,740,797 A | 4/1998 | Dickson |
| 5,765,558 A | 6/1998 | Psaros et al. |
| 5,803,065 A | 9/1998 | Zdrojkowski et al. |
| 5,806,512 A | 9/1998 | Abramov et al. |
| 5,807,245 A | 9/1998 | Aldestam et al. |
| 5,810,000 A | 9/1998 | Stevens |
| 5,813,401 A | 9/1998 | Radcliff et al. |
| 5,814,086 A | 9/1998 | Hirschberg et al. |
| 5,868,133 A | 2/1999 | DeVries et al. |
| 5,876,352 A | 3/1999 | Weismann |
| 5,878,744 A | 3/1999 | Pfeiffer |
| 5,881,725 A | 3/1999 | Hoffman et al. |
| 5,906,203 A | 5/1999 | Klockseth et al. |
| 5,911,218 A | 6/1999 | DiMarco |
| 5,915,381 A | 6/1999 | Nord |
| 5,931,160 A | 8/1999 | Gilmore et al. |
| 5,931,162 A | 8/1999 | Christian |
| 5,937,853 A | 8/1999 | Strom |
| 5,944,680 A | 8/1999 | Christopherson |
| 5,970,975 A | 10/1999 | Estes et al. |
| 5,996,580 A | 12/1999 | Swann |
| 6,015,388 A | 1/2000 | Sackner et al. |
| 6,019,100 A | 2/2000 | Alving et al. |
| 6,029,664 A | 2/2000 | Zdrojkowski et al. |
| 6,068,602 A | 5/2000 | Tham et al. |
| 6,085,747 A | 7/2000 | Axe |
| 6,095,140 A | 8/2000 | Poon et al. |
| 6,109,260 A | 8/2000 | Bathe |
| 6,112,744 A | 9/2000 | Hognelid |
| 6,131,571 A | 10/2000 | Lampotang et al. |
| 6,131,572 A | 10/2000 | Heinonen |
| 6,135,105 A | 10/2000 | Lampotang et al. |
| 6,148,814 A | 11/2000 | Clemmer et al. |
| 6,152,129 A | 11/2000 | Berthon Jones |
| 6,152,133 A | 11/2000 | Psaros et al. |
| 6,152,135 A | 11/2000 | DeVries et al. |
| 6,155,257 A | 12/2000 | Lurie et al. |
| 6,158,432 A | 12/2000 | Biondi et al. |
| 6,158,433 A | 12/2000 | Ong et al. |
| 6,192,885 B1 | 2/2001 | Jalde |
| 6,196,222 B1 | 3/2001 | Heinonen et al. |
| 6,213,119 B1 | 4/2001 | Brydon et al. |
| 6,230,708 B1 | 5/2001 | Radko |
| 6,257,234 B1 | 7/2001 | Sun |
| 6,260,549 B1 | 7/2001 | Sosiak |
| 6,279,569 B1 | 8/2001 | Berthon Jones |
| 6,279,574 B1 | 8/2001 | Richardson et al. |
| 6,305,372 B1 | 10/2001 | Servidio |
| 6,305,374 B1 | 10/2001 | Zdrojkowski et al. |
| 6,308,703 B1 | 10/2001 | Alving et al. |
| 6,308,706 B1 | 10/2001 | Lammers et al. |
| 6,343,603 B1 | 2/2002 | Tuck et al. |
| 6,345,619 B1 | 2/2002 | Finn |
| 6,360,740 B1 | 3/2002 | Ward et al. |
| 6,390,091 B1 | 5/2002 | Banner et al. |
| 6,390,988 B1 | 5/2002 | Robinson |
| 6,408,847 B1 | 6/2002 | Nuckols et al. |
| 6,412,482 B1 | 7/2002 | Rowe |
| 6,425,392 B1 | 7/2002 | Sosiak |
| 6,439,229 B1 | 8/2002 | Du et al. |
| 6,450,968 B1 | 9/2002 | Wallen et al. |
| 6,461,315 B1 | 10/2002 | Gattinoni |
| 6,463,930 B2 | 10/2002 | Biondi et al. |
| 6,467,477 B1 | 10/2002 | Frank |
| 6,467,479 B1 | 10/2002 | Albert et al. |
| 6,484,719 B1 | 11/2002 | Berthon Jones |
| 6,488,634 B1 | 12/2002 | Rapoport |
| 6,494,201 B1 | 12/2002 | Welik |
| 6,510,851 B2 | 1/2003 | Rydin |
| 6,516,800 B1 | 2/2003 | Bowden |
| 6,523,538 B1 | 2/2003 | Wikfeldt |
| 6,526,970 B2 | 3/2003 | DeVries et al. |
| 6,532,956 B2 | 3/2003 | Hill |
| 6,532,957 B2 | 3/2003 | Berthon Jones |
| 6,532,959 B1 | 3/2003 | Berthon Jones |
| 6,533,730 B2 | 3/2003 | Stroem |
| 6,539,938 B2 | 4/2003 | Weinstein et al. |
| 6,539,940 B2 | 4/2003 | Zdrojkowski et al. |
| 6,547,743 B2 | 4/2003 | Brydon |
| 6,553,992 B1 | 4/2003 | Berthon Jones et al. |
| 6,557,553 B1 | 5/2003 | Borrello |
| 6,564,798 B1 | 5/2003 | Jalde |
| 6,571,796 B2 | 6/2003 | Banner et al. |
| 6,575,163 B1 | 6/2003 | Berthon Jones |
| 6,575,164 B1 | 6/2003 | Jaffe et al. |
| 6,578,575 B1 | 6/2003 | Jonson |
| 6,581,599 B1 | 6/2003 | Stenzler |
| 6,584,973 B1 | 7/2003 | Biondi |
| 6,588,423 B1 | 7/2003 | Sinderby |
| 6,589,188 B1 | 7/2003 | Street |

(56) References Cited

U.S. PATENT DOCUMENTS

| | | |
|---|---|---|
| 6,595,213 B2 | 7/2003 | Bennarsten |
| 6,601,583 B2 | 8/2003 | Pessala et al. |
| 6,609,517 B1 | 8/2003 | Estes et al. |
| 6,609,518 B2 | 8/2003 | Lamb |
| 6,622,726 B1 | 9/2003 | Du |
| 6,626,175 B2 | 9/2003 | Jafari et al. |
| 6,626,176 B1 | 9/2003 | Madaus |
| 6,631,716 B1 | 10/2003 | Robinson et al. |
| 6,631,717 B1 | 10/2003 | Rich et al. |
| 6,644,310 B1 | 11/2003 | Delache et al. |
| 6,651,652 B1 | 11/2003 | Ward |
| 6,651,657 B1 | 11/2003 | Manigel |
| 6,659,101 B2 | 12/2003 | Berthon Jones |
| 6,659,961 B2 | 12/2003 | Robinson |
| 6,663,574 B2 | 12/2003 | Faram |
| 6,668,829 B2 | 12/2003 | Biondi et al. |
| 6,679,258 B1 | 1/2004 | Strom |
| 6,681,643 B2 | 1/2004 | Heinonen |
| 6,688,307 B2 | 2/2004 | Berthon Jones |
| 6,689,091 B2 | 2/2004 | Bui et al. |
| 6,694,978 B1 | 2/2004 | Bennarsten |
| 6,709,405 B2 | 3/2004 | Jonson |
| 6,722,360 B2 | 4/2004 | Doshi |
| 6,726,598 B1 | 4/2004 | Jarvis et al. |
| 6,739,336 B1 | 5/2004 | Jalde |
| 6,745,771 B2 | 6/2004 | Castor et al. |
| 6,745,773 B1 | 6/2004 | Gobel |
| 6,752,766 B2 | 6/2004 | Kowallik et al. |
| 6,752,772 B2 | 6/2004 | Kahn |
| 6,755,193 B2 | 6/2004 | Berthon Jones et al. |
| 6,758,216 B1 | 7/2004 | Berthon Jones et al. |
| 6,763,829 B2 | 7/2004 | Jaffe et al. |
| 6,786,217 B2 | 9/2004 | Stenzler |
| 6,796,305 B1 | 9/2004 | Banner et al. |
| 6,805,118 B2 | 10/2004 | Brooker et al. |
| 6,810,876 B2 | 11/2004 | Jones |
| 6,814,073 B2 | 11/2004 | Wickham |
| 6,814,075 B2 | 11/2004 | Boussignac |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,832,609 B2 | 12/2004 | Wright |
| 6,834,647 B2 | 12/2004 | Blair et al. |
| 6,837,241 B2 | 1/2005 | Samzelius |
| 6,837,242 B2 | 1/2005 | Younes |
| 6,840,240 B1 | 1/2005 | Berthon Jones et al. |
| 6,851,427 B1 | 2/2005 | Nashed |
| 6,854,462 B2 | 2/2005 | Berthon-Jones |
| 6,860,264 B2 | 3/2005 | Christopher |
| 6,860,265 B1 | 3/2005 | Emerson |
| 6,860,858 B2 | 3/2005 | Green et al. |
| 6,877,511 B2 | 4/2005 | DeVries et al. |
| 6,880,556 B2 | 4/2005 | Uchiyama |
| 6,910,480 B1 | 6/2005 | Berthon Jones |
| 6,920,875 B1 | 7/2005 | Hill et al. |
| 6,932,084 B2 | 8/2005 | Estes |
| 6,948,497 B2 | 9/2005 | Zdrojkowski et al. |
| 6,976,487 B1 | 12/2005 | Melker et al. |
| 6,990,980 B2 | 1/2006 | Richey, II |
| 6,997,881 B2 | 2/2006 | Green et al. |
| 7,000,612 B2 | 2/2006 | Jafari et al. |
| 7,001,339 B2 | 2/2006 | Lin |
| 7,001,340 B2 | 2/2006 | Lin |
| 7,011,091 B2 | 3/2006 | Hill et al. |
| 7,013,892 B2 | 3/2006 | Estes et al. |
| 7,017,574 B2 | 3/2006 | Biondi et al. |
| 7,018,341 B2 | 3/2006 | Wright |
| 7,040,321 B2 | 5/2006 | Gobel et al. |
| 7,051,736 B2 | 5/2006 | Banner et al. |
| 7,055,522 B2 | 6/2006 | Jones |
| 7,066,173 B2 | 6/2006 | Banner et al. |
| 7,066,176 B2 | 6/2006 | Jaffe et al. |
| 7,080,646 B2 | 7/2006 | Wiesmann et al. |
| 7,086,098 B2 | 8/2006 | Sallvin |
| 7,089,936 B2 | 8/2006 | Madaus |
| 7,100,607 B2 | 9/2006 | Zdrojkowski et al. |
| 7,100,609 B2 | 9/2006 | Berthon Jones et al. |
| 7,121,277 B2 | 10/2006 | Ström |
| 7,128,069 B2 | 10/2006 | Farrugia et al. |
| 7,137,389 B2 | 11/2006 | Berthon Jones |
| 7,152,598 B2 | 12/2006 | Morris |
| 7,156,095 B2 | 1/2007 | Melker et al. |
| 7,159,588 B2 | 1/2007 | Wickham |
| 7,162,296 B2 | 1/2007 | Leonhardt et al. |
| 7,168,429 B2 | 1/2007 | Matthews |
| 7,191,780 B2 | 3/2007 | Faram |
| 7,210,478 B2 | 5/2007 | Banner et al. |
| 7,226,427 B2 | 6/2007 | Steen |
| 7,246,618 B2 | 7/2007 | Habashi |
| 7,255,103 B2 | 8/2007 | Bassin |
| 7,275,540 B2 | 10/2007 | Bolam et al. |
| 7,305,988 B2 | 12/2007 | Acker |
| 7,334,578 B2 | 2/2008 | Biondi et al. |
| 7,334,581 B2 | 2/2008 | Doshi |
| 7,347,205 B2 | 3/2008 | Levi |
| 7,363,925 B2 | 4/2008 | Pagan |
| 7,367,337 B2 | 5/2008 | Berthon Jones et al. |
| 7,422,015 B2 | 9/2008 | Delisle et al. |
| 7,425,201 B2 | 9/2008 | Euliano et al. |
| 7,431,035 B2 | 10/2008 | Mizuta |
| 7,445,006 B2 | 11/2008 | Dhuper et al. |
| 7,464,711 B2 | 12/2008 | Flodin |
| 7,484,508 B2 | 2/2009 | Younes |
| 7,487,774 B2 | 2/2009 | Acker |
| 7,487,775 B2 | 2/2009 | Mashak |
| 7,487,778 B2 | 2/2009 | Freitag |
| 7,509,957 B2 | 3/2009 | Duquette et al. |
| 7,523,752 B2 | 4/2009 | Montgomery et al. |
| 7,530,353 B2 | 5/2009 | Choncholas et al. |
| 7,549,421 B2 | 6/2009 | Levi et al. |
| 7,556,038 B2 | 7/2009 | Kirby et al. |
| 7,559,326 B2 | 7/2009 | Smith et al. |
| 7,572,225 B2 | 8/2009 | Stahmann et al. |
| 7,574,246 B2 | 8/2009 | Krebs et al. |
| 7,584,752 B2 | 9/2009 | Garber et al. |
| 7,588,033 B2 | 9/2009 | Wondka |
| 7,588,543 B2 | 9/2009 | Euliano et al. |
| 7,594,508 B2 | 9/2009 | Doyle |
| 7,607,432 B2 | 10/2009 | Sullivan |
| 7,610,914 B2 | 11/2009 | Bolam et al. |
| 7,617,821 B2 | 11/2009 | Hughes |
| 7,617,825 B2 | 11/2009 | Pedemonte |
| 7,624,736 B2 | 12/2009 | Borody |
| 7,634,998 B1 | 12/2009 | Fenley |
| 7,644,713 B2 | 1/2010 | Berthon Jones |
| 7,669,594 B2 | 3/2010 | Downie |
| 7,669,598 B2 | 3/2010 | Rick et al. |
| 7,678,061 B2 | 3/2010 | Lee et al. |
| 7,694,682 B2 | 4/2010 | Petersen et al. |
| 7,708,015 B2 | 5/2010 | Seeger |
| 7,717,110 B2 | 5/2010 | Kane et al. |
| 7,721,736 B2 | 5/2010 | Urias et al. |
| 7,722,546 B2 | 5/2010 | Madaus et al. |
| 7,727,160 B2 | 6/2010 | Green et al. |
| 7,731,663 B2 | 6/2010 | Averina et al. |
| 7,775,207 B2 | 8/2010 | Jaffe et al. |
| 7,798,145 B2 | 9/2010 | Weismann et al. |
| 7,802,571 B2 | 9/2010 | Tehrani |
| 7,809,442 B2 | 10/2010 | Bolea et al. |
| 7,810,496 B2 | 10/2010 | Estes |
| 7,810,497 B2 | 10/2010 | Pittman |
| 7,814,906 B2 | 10/2010 | Moretti |
| 7,819,815 B2 | 10/2010 | Younes |
| 7,841,341 B2 | 11/2010 | Dhuper et al. |
| 7,841,343 B2 | 11/2010 | Deane |
| 7,865,244 B2 | 1/2011 | Giftakis et al. |
| 7,866,318 B2 | 1/2011 | Bassin |
| 7,891,353 B2 | 2/2011 | Chalvignac |
| 7,905,231 B2 | 3/2011 | Chalvignac |
| 7,914,459 B2 | 3/2011 | Green |
| 7,918,226 B2 | 4/2011 | Acker |
| 7,934,499 B2 | 5/2011 | Berthon-Jones |
| 7,934,500 B2 | 5/2011 | Madaus |
| 7,938,114 B2 | 5/2011 | Matthews |

(56) References Cited

U.S. PATENT DOCUMENTS

| | | |
|---|---|---|
| 7,942,823 B2 | 5/2011 | Wright |
| 7,984,712 B2 | 7/2011 | Soliman |
| 8,015,974 B2 | 9/2011 | Christopher |
| 8,020,555 B2 | 9/2011 | Rapoport |
| 8,020,558 B2 | 9/2011 | Christopher |
| 8,021,309 B2 | 9/2011 | Zilberg |
| 8,025,052 B2 | 9/2011 | Matthews |
| 8,051,852 B2 | 11/2011 | Bassin |
| 8,061,354 B2 | 11/2011 | Schneider |
| 8,066,003 B2 | 11/2011 | Cong |
| 8,122,883 B2 | 2/2012 | Banner |
| 8,136,521 B2 | 3/2012 | Matthews |
| 8,157,743 B2 | 4/2012 | Schaetzl |
| 8,160,817 B2 | 4/2012 | Ranieri |
| 8,186,344 B2 | 5/2012 | Bonassa |
| 8,220,456 B2 | 7/2012 | Kane |
| 8,225,789 B2 | 7/2012 | Berthon-Jones |
| 8,261,742 B2 | 9/2012 | Strothmann |
| 8,312,879 B2 | 11/2012 | Choncholas |
| 8,316,847 B2 | 11/2012 | Hallett |
| 8,353,844 B2 | 1/2013 | Jin |
| 8,381,724 B2 | 2/2013 | Bowen |
| 8,381,729 B2 | 2/2013 | Freitag |
| 8,388,548 B2 | 3/2013 | Green |
| 8,397,720 B2 | 3/2013 | Eger |
| 8,408,205 B2 | 4/2013 | Madaus |
| 8,424,524 B2 | 4/2013 | Heinonen |
| 8,443,801 B2 | 5/2013 | Soliman |
| 8,485,982 B2 | 7/2013 | Gavish |
| 8,522,781 B2 | 9/2013 | Schneider |
| 8,528,553 B2 | 9/2013 | Wysocki |
| 8,550,077 B2 | 10/2013 | Chatburn |
| 8,555,880 B2 | 10/2013 | Boring |
| 8,573,205 B2 | 11/2013 | Habashi |
| 8,573,207 B2 | 11/2013 | Gutierrez |
| 8,603,006 B2 | 12/2013 | Mulqueeny |
| 8,617,083 B2 | 12/2013 | Euliano |
| 8,646,447 B2 | 2/2014 | Martin |
| 8,652,065 B2 | 2/2014 | Titchener |
| 8,672,858 B2 | 3/2014 | Euliano |
| 8,689,791 B2 | 4/2014 | Hayek |
| 8,695,597 B2 | 4/2014 | Glaw |
| 8,701,665 B2 | 4/2014 | Tehrani |
| 8,707,953 B2 | 4/2014 | Wickham |
| 8,783,247 B2 | 7/2014 | Newman, Jr. |
| 8,826,906 B2 | 9/2014 | Bassin |
| 8,869,795 B2 | 10/2014 | Bassin |
| 8,893,717 B2 | 11/2014 | Montgomery |
| 8,899,231 B2 | 12/2014 | Bassin |
| 8,899,232 B2 | 12/2014 | Farrugia |
| 8,910,632 B2 | 12/2014 | Tiedje |
| 8,920,333 B2 | 12/2014 | Younes |
| 8,925,545 B2 | 1/2015 | Wondka |
| 8,944,057 B2 | 2/2015 | Hill |
| 8,985,107 B2 | 3/2015 | Viertiö-Oja |
| 8,985,109 B2 | 3/2015 | Bateman |
| 9,016,277 B2 | 4/2015 | Kniewasser |
| 9,078,984 B2 | 7/2015 | Poon |
| 9,114,222 B2 | 8/2015 | Bliss |
| 9,192,323 B2 | 11/2015 | Heyer |
| 9,205,210 B2 | 12/2015 | Bassin |
| 9,216,262 B2 | 12/2015 | Desforges |
| 9,220,856 B2 | 12/2015 | Martin |
| 9,238,114 B2 | 1/2016 | Eger |
| 9,259,544 B2 | 2/2016 | Kane |
| 9,272,106 B2 | 3/2016 | Sibenaller |
| 9,295,796 B2 | 3/2016 | Eklund |
| 9,295,797 B2 | 3/2016 | Shissler |
| 9,320,863 B2 | 4/2016 | Balko |
| 9,333,312 B2 | 5/2016 | Cardelius |
| 9,392,963 B2 | 7/2016 | Krans |
| 9,392,964 B2 | 7/2016 | Mulqueeny |
| 9,504,795 B2 | 11/2016 | Bassin |
| 9,555,204 B2 | 1/2017 | Rahlf |
| 9,592,356 B2 | 3/2017 | Truschel |
| 9,597,467 B2 | 3/2017 | Zheng |
| 9,636,474 B2 | 5/2017 | Mulqueeny |
| 9,655,544 B2 | 5/2017 | Stenqvist |
| 9,682,208 B2 | 6/2017 | Ramanan |
| 9,713,690 B2 | 7/2017 | Somaiya |
| 9,757,270 B2 | 9/2017 | Carrubba |
| 9,827,387 B2 | 11/2017 | Schneider |
| 9,839,760 B2 | 12/2017 | Bonassa |
| 9,848,831 B2 | 12/2017 | Nonaka |
| 9,925,346 B2 | 3/2018 | Dong |
| 9,968,750 B2 | 5/2018 | Sinderby |
| 9,980,943 B2 | 5/2018 | Burkin |
| 9,987,444 B2 | 6/2018 | Colbaugh |
| 9,987,445 B2 | 6/2018 | Ahmad |
| 10,004,862 B2 | 6/2018 | Armitstead |
| 10,022,084 B2 | 7/2018 | Nonaka |
| 10,022,512 B2 | 7/2018 | Tiedje |
| 10,065,007 B2 | 9/2018 | Troili |
| 10,137,266 B2 | 11/2018 | Shelly |
| 10,165,966 B2 | 1/2019 | Banner |
| 10,179,218 B2 | 1/2019 | Ahmad |
| 10,207,068 B2 | 2/2019 | Jafari |
| 10,293,126 B2 | 5/2019 | Berry Ann |
| 10,314,515 B2 | 6/2019 | Colman |
| 10,335,566 B2 | 7/2019 | Kulstad |
| 10,342,457 B2 | 7/2019 | Spencer |
| 10,357,624 B2 | 7/2019 | Van Der Staay |
| 11,191,447 B2 * | 12/2021 | Wang .................. A61B 5/7221 |
| 11,224,379 B2 * | 1/2022 | Vicario ............ A61M 16/0057 |
| 2001/0004893 A1 | 6/2001 | Biondi et al. |
| 2001/0007255 A1 | 7/2001 | Stumpf |
| 2002/0023640 A1 | 2/2002 | Nightengale |
| 2002/0026941 A1 | 3/2002 | Biondi et al. |
| 2002/0046753 A1 | 4/2002 | Lamb |
| 2002/0073993 A1 | 6/2002 | Weinstein et al. |
| 2002/0174866 A1 | 11/2002 | Orr et al. |
| 2002/0185126 A1 | 12/2002 | Krebs |
| 2002/0195105 A1 | 12/2002 | Blue et al. |
| 2003/0010339 A1 | 1/2003 | Banner et al. |
| 2003/0034031 A1 | 2/2003 | Lev et al. |
| 2003/0037786 A1 | 2/2003 | Biondi et al. |
| 2003/0125662 A1 | 7/2003 | Bui |
| 2003/0131848 A1 | 7/2003 | Stenzler |
| 2003/0136402 A1 | 7/2003 | Jiang et al. |
| 2003/0145853 A1 | 8/2003 | Muellner |
| 2003/0154979 A1 | 8/2003 | Berthon Jones |
| 2003/0159695 A1 | 8/2003 | Younes |
| 2003/0172929 A1 | 9/2003 | Muellner |
| 2003/0178024 A1 | 9/2003 | Allan et al. |
| 2003/0192544 A1 | 10/2003 | Berthon Jones et al. |
| 2004/0016431 A1 | 1/2004 | Preveyraud |
| 2004/0050387 A1 | 3/2004 | Younes |
| 2004/0103896 A1 | 6/2004 | Jafari et al. |
| 2004/0159323 A1 | 8/2004 | Schmidt et al. |
| 2004/0187864 A1 | 9/2004 | Adams |
| 2004/0194779 A1 | 10/2004 | Doshi |
| 2004/0194780 A1 | 10/2004 | Doshi |
| 2004/0200477 A1 | 10/2004 | Bleys et al. |
| 2004/0206355 A1 | 10/2004 | Berthon Jones et al. |
| 2004/0221847 A1 | 11/2004 | Berthon Jones et al. |
| 2004/0231670 A1 | 11/2004 | Bassin |
| 2005/0022809 A1 | 2/2005 | Wondka |
| 2005/0027252 A1 | 2/2005 | Boukas |
| 2005/0061318 A1 | 3/2005 | Faram |
| 2005/0076907 A1 | 4/2005 | Stenzler |
| 2005/0098179 A1 | 5/2005 | Burton et al. |
| 2005/0103331 A1 | 5/2005 | Wedemeyer |
| 2005/0109339 A1 | 5/2005 | Stahmann et al. |
| 2005/0109340 A1 | 5/2005 | Tehrani |
| 2005/0126565 A1 | 6/2005 | Huang |
| 2005/0133028 A1 | 6/2005 | Pagan |
| 2005/0199237 A1 | 9/2005 | Lurie |
| 2005/0217671 A1 | 10/2005 | Fisher et al. |
| 2005/0241639 A1 | 11/2005 | Zilberg |
| 2005/0263152 A1 | 12/2005 | Fong |
| 2005/0279358 A1 | 12/2005 | Richey, II |
| 2005/0284469 A1 | 12/2005 | Tobia et al. |
| 2006/0011195 A1 | 1/2006 | Zarychta |
| 2006/0032497 A1 | 2/2006 | Doshi |

(56) References Cited

U.S. PATENT DOCUMENTS

| | | |
|---|---|---|
| 2006/0094972 A1 | 5/2006 | Drew |
| 2006/0102180 A1 | 5/2006 | Berthon Jones |
| 2006/0162727 A1 | 7/2006 | Biondi et al. |
| 2006/0178245 A1 | 8/2006 | Schiller et al. |
| 2006/0201507 A1 | 9/2006 | Breen |
| 2006/0249148 A1 | 11/2006 | Younes |
| 2006/0249155 A1 | 11/2006 | Gambone |
| 2006/0272642 A1 | 12/2006 | Chalvignac |
| 2006/0276718 A1 | 12/2006 | Madaus et al. |
| 2006/0278221 A1 | 12/2006 | Schermeier et al. |
| 2006/0278224 A1 | 12/2006 | Shaffer et al. |
| 2006/0283450 A1 | 12/2006 | Shissler et al. |
| 2006/0283451 A1 | 12/2006 | Albertelli |
| 2007/0000494 A1 | 1/2007 | Banner et al. |
| 2007/0017518 A1 | 1/2007 | Farrugia et al. |
| 2007/0028921 A1 | 2/2007 | Banner et al. |
| 2007/0044796 A1 | 3/2007 | Zdrojkowski et al. |
| 2007/0062529 A1 | 3/2007 | Choncholas et al. |
| 2007/0113843 A1 | 5/2007 | Hughes |
| 2007/0144523 A1 | 6/2007 | Bolam et al. |
| 2007/0151563 A1 | 7/2007 | Ozaki et al. |
| 2007/0163590 A1 | 7/2007 | Bassin |
| 2007/0181122 A1 | 8/2007 | Mulier |
| 2007/0186928 A1 | 8/2007 | Be'Eri |
| 2007/0191787 A1 | 8/2007 | Lim et al. |
| 2007/0208267 A1 | 9/2007 | Schmid et al. |
| 2007/0221222 A1 | 9/2007 | Lurie |
| 2007/0225623 A1 | 9/2007 | Freeman |
| 2007/0227538 A1 | 10/2007 | Scholler et al. |
| 2007/0227539 A1 | 10/2007 | Schwaibold et al. |
| 2007/0267015 A1 | 11/2007 | Thoemmes et al. |
| 2007/0272243 A1 | 11/2007 | Sherman et al. |
| 2007/0277825 A1 | 12/2007 | Bordewick et al. |
| 2008/0000471 A1 | 1/2008 | Bolam et al. |
| 2008/0000475 A1 | 1/2008 | Hill |
| 2008/0000478 A1 | 1/2008 | Matthiessen et al. |
| 2008/0011294 A1 | 1/2008 | Heesch et al. |
| 2008/0017198 A1 | 1/2008 | Ivri |
| 2008/0029096 A1 | 2/2008 | Kollmeyer et al. |
| 2008/0033304 A1 | 2/2008 | Dalal et al. |
| 2008/0035146 A1 | 2/2008 | Crabb |
| 2008/0041382 A1 | 2/2008 | Matthews et al. |
| 2008/0092894 A1 | 4/2008 | Nicolazzi et al. |
| 2008/0097234 A1 | 4/2008 | Nicolazzi et al. |
| 2008/0115786 A1 | 5/2008 | Sinderby et al. |
| 2008/0125828 A1 | 5/2008 | Ignagni et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0163872 A1 | 7/2008 | Negele et al. |
| 2008/0178880 A1 | 7/2008 | Christopher et al. |
| 2008/0178882 A1 | 7/2008 | Christopher et al. |
| 2008/0216833 A1 | 9/2008 | Pujol et al. |
| 2008/0251078 A1 | 10/2008 | Buckley et al. |
| 2008/0257337 A1 | 10/2008 | Denyer et al. |
| 2008/0275513 A1 | 11/2008 | Lattner et al. |
| 2008/0276940 A1 | 11/2008 | Fuhrman et al. |
| 2008/0281219 A1 | 11/2008 | Glickman et al. |
| 2008/0283060 A1 | 11/2008 | Bassin |
| 2008/0283061 A1 | 11/2008 | Tiedje |
| 2008/0294060 A1 | 11/2008 | Haro et al. |
| 2008/0295839 A1 | 12/2008 | Habashi |
| 2008/0295840 A1 | 12/2008 | Glaw |
| 2009/0013999 A1 | 1/2009 | Bassin |
| 2009/0056709 A1 | 3/2009 | Worsoff |
| 2009/0120439 A1 | 5/2009 | Goebel |
| 2010/0116270 A1 | 5/2010 | Edwards et al. |
| 2010/0125227 A1 | 5/2010 | Bird |
| 2010/0186744 A1 | 7/2010 | Andrieux |
| 2010/0229863 A1 | 9/2010 | Enk |
| 2010/0236551 A1 | 9/2010 | Enk |
| 2010/0263669 A1 | 10/2010 | Bowsher |
| 2011/0011403 A1 | 1/2011 | Hannah et al. |
| 2013/0284172 A1* | 10/2013 | Doyle ............... A61M 16/0051 128/204.23 |
| 2014/0123979 A1* | 5/2014 | Doyle ............... G16H 50/20 128/204.23 |
| 2016/0045694 A1* | 2/2016 | Esmaeil-zadeh-azar ................... A61B 5/7239 128/204.23 |
| 2016/0228282 A1 | 8/2016 | Carrubba |
| 2016/0243324 A1 | 8/2016 | Doyle |
| 2016/0250427 A1 | 9/2016 | Jafari |
| 2016/0256643 A1 | 9/2016 | Graboi |
| 2016/0256656 A1 | 9/2016 | Glenn |
| 2016/0354566 A1 | 12/2016 | Thiessen |
| 2017/0095627 A1 | 4/2017 | Jafari |
| 2017/0164872 A1 | 6/2017 | Sanborn |
| 2017/0182269 A1 | 6/2017 | Masic |
| 2017/0296765 A1 | 10/2017 | Dong |
| 2018/0036500 A1 | 2/2018 | Esmaeil-zadeh-azar |
| 2018/0193578 A1 | 7/2018 | Glenn |
| 2018/0207378 A1 | 7/2018 | Masic |
| 2018/0207379 A1 | 7/2018 | Masic |
| 2018/0304034 A1 | 10/2018 | Vicario et al. |
| 2018/0325459 A1 | 11/2018 | Nakai |
| 2019/0143058 A1 | 5/2019 | Gardner |
| 2019/0274585 A1 | 9/2019 | Milne |
| 2019/0344034 A1 | 11/2019 | Li |

FOREIGN PATENT DOCUMENTS

| | | |
|---|---|---|
| EP | 1005830 | 6/2000 |
| EP | 996358 | 1/2002 |
| EP | 1277435 | 1/2003 |
| WO | WO 2008/008659 | 1/2008 |
| WO | WO 2008/021222 | 2/2008 |
| WO | WO 2008/113752 | 9/2008 |
| WO | WO 2009/060330 | 5/2009 |

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Boitano, Louis J., "An Evaluation of Home Volume Ventilators That Support OpenCircuit Mouthpiece Ventilation", Respiratory Care, Nov. 2005, vol. 50, No. 11, pp. 1457-1461.
Puritan Bennett 980 Series Ventilator Operator's Manual, Covidien, Jan. 29, 2014, Part. No. 10077893 A Jan. 2014, 506 pages.
PCT International Search Report and Written Opinion in International Application PCT/US2019/032280, dated Jul. 30, 2019, 15 pgs.

* cited by examiner

SYSTEMS AND METHODS FOR AUTOMATIC CYCLING OR CYCLING DETECTION

CROSS-REFERENCE TO RELATED APPLICATIONS

This application claims the benefit of U.S. Provisional Application Ser. No. 62/740,740, filed Oct. 3, 2018, the complete disclosure of which is hereby incorporated by reference in its entirety.

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes.

It is with respect to this general technical environment that aspects of the present technology disclosed herein have been contemplated. Furthermore, although a general environment has been discussed, it should be understood that the examples described herein should not be limited to the general environment identified herein.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Aspects of the disclosure relate to providing novel systems and methods for cycling or ending exhalation during mechanical ventilation of a patient. More specifically, this disclosure describes systems and methods for cycling ventilation based on estimated muscle pressure.

In an aspect, a ventilator system is provided. The ventilator system includes at least one sensor, a gas-delivery system configured to deliver ventilation gases to a patient, at least one processor, and at least one memory comprising computer-executable instructions that when executed by the at least one processor cause the ventilator system to perform various operations. The operations include receiving one or more sensor measurements from the at least one sensor during inhalation of the patient and, based on the one or more sensor measurements, estimating a muscle pressure ($P_{MUS}$) of the patient during the inhalation of the patient. Based on the estimate of $P_{MUS}$, the operations further include determining a $P_{MUS}$-based metric and, in response to determining that the $P_{MUS}$-based metric meets a cycling threshold, determining a patient intention to cycle. Additionally, the operations include evaluating one or more characteristics of the patient intention to cycle and, when the one or more characteristics of the patient intention to cycle are abnormal, determining a missed cycling effort. In response to the missed cycling effort, the operations include performing an action.

In another aspect, a method of determining a patient intention to cycle is provided. The method includes delivering spontaneous ventilation to a patient and, based on a target setting for the spontaneous ventilation, determining a percent support setting. The method further includes temporarily switching to a proportional assist (PA) breath type and delivering at least one PA breath based on the determined percent support setting. During the at least one PA breath, the method includes receiving one or more sensor measurements from the at least one sensor and, based on the one or more sensor measurements, estimating a muscle pressure ($P_{MUS}$) of the patient. In response to determining that the $P_{MUS}$ meets a cycling threshold, the method includes determining a patient intention to cycle.

In yet another aspect, a method for detecting a patient intention to cycle during spontaneous ventilation of the patient on a ventilator is provided. The method includes monitoring at least one parameter of the patient receiving spontaneous ventilation based on one or more received non-invasive sensor measurements during inhalation and, based on the one or more received non-invasive sensor measurements, estimating a muscle pressure ($P_{MUS}$) of the patient during the inhalation. The method further includes comparing a $P_{MUS}$-based metric to a cycling threshold and determining that the $P_{MUS}$-based metric meets the cycling threshold to identify a patient intention to cycle. In response to identifying the patient intention to cycle, the method includes evaluating one or more characteristics of the patient intention to cycle and, when the one or more characteristics of the patient intention to cycle are abnormal, determining a missed cycling effort. Additionally, the method includes performing an action in response to the missed cycling effort.

It is to be understood that both the foregoing general description and the following detailed description are exemplary and explanatory and are intended to provide further explanation of the disclosure as claimed.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

DETAILED DESCRIPTION

Figure 1:
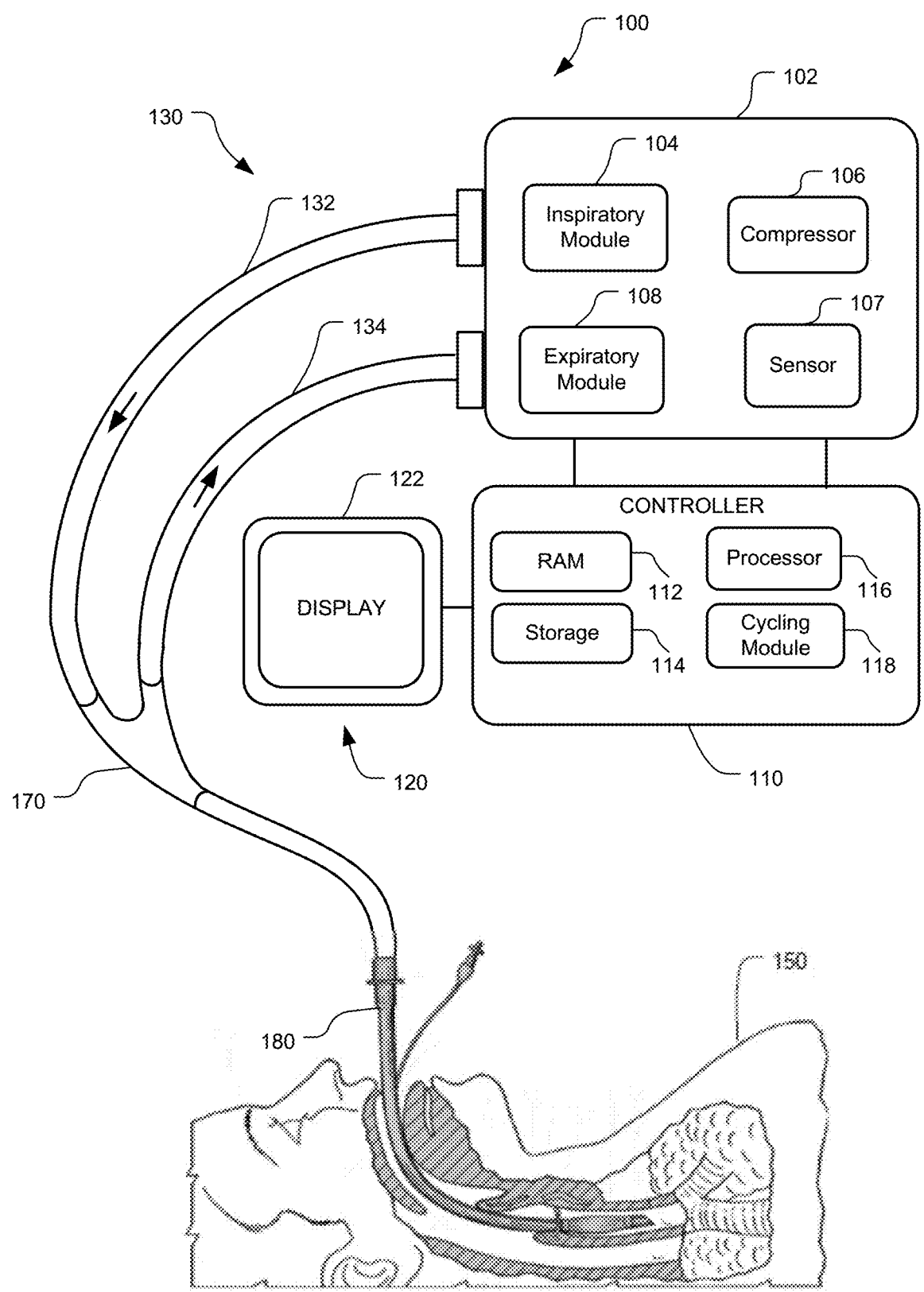
FIG. 1 is a schematic diagram illustrating a ventilator capable of detecting patient exhalation or cycling efforts based on estimated muscle pressure, in accordance with aspects of the disclosure.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and flow rates. Ventilators capable of operating independently of external sources of pressurized air are also available.

As each patient may require a different ventilation strategy, modern ventilators can be customized for the particular needs of an individual patient. For example, several different ventilator modes, breath types, and/or settings have been created to provide better ventilation for patients in various different scenarios, such as mandatory ventilation modes and assist control ventilation modes. Mandatory ventilation modes provide ventilator-initiated triggering and cycling, whereas assist control modes allow a spontaneously breathing patient to trigger inspiration during ventilation. In a spontaneous mode of ventilation, the ventilator triggers inspiration upon the detection of patient demand or patient effort to inhale and cycles or initiates expiration when a predetermined threshold is met or when a patient demand or effort for exhalation is detected.

The response performance of a medical ventilator to a patient cycle from inhalation into exhalation represents an important characteristic of a medical ventilator. A ventilator's exhalation trigger or cycle response impacts the patient's work of breathing and the overall patient-ventilator synchrony. The exhalation cycle response performance of a ventilator is a function of a patient's expiratory behavior (breathing effort magnitude and timing characteristics) as well as the ventilator's gas delivery dynamics and flow control parameters (actuator response, dead bands, etc.).

Triggering delay time, cycling delay time, and asynchrony index are among key parameters that are used to measure the patient-ventilator synchrony. The asynchrony index is the ratio between the number of asynchronous events and the total respiratory rate. Miss-cycling is also considered as one of the factors that increases the patient-ventilator asynchrony index. Several different factors cause asynchrony events, such as variation in patient's breathing pattern, muscle strength, respiratory mechanics, ventilator performance, and ventilator characteristics.

Traditionally the inspiration is cycled off based on an $E_{SENS}$ threshold, which may be a set percentage (normally 25%) of the peak inspiratory flow or a set flow value on many intensive care ventilators. This adjustable value, however, is often not optimal, resulting in patient-ventilator expiratory asynchrony. Expiratory asynchrony has been shown to be a clinical issue in the patients with partial ventilatory support. Under the expiratory asynchrony situation, the termination of the ventilator flow occurs either before or after patients stop their inspiratory efforts. When the termination of the ventilator flow falls behind the end of the patient inspiratory effort (i.e. delayed cycling), the patient recruits his or her expiratory muscles to "fight" against the ventilator flow, which increases expiratory workload, resulting in intrinsic PEEP. When the termination of the ventilator flow occurs before the end of patient inspiratory effort (i.e. premature cycling), the patient inspiratory muscle work continues into or even throughout the ventilator's expiratory phase, thus resulting in inefficient inspiratory muscle work. For PA, TC, PS or VS, to address premature cycling, the percent support setting may be increased or the $E_{SENS}$ setting may be decreased (less sensitive). Alternatively, for PA, TC, PS or VS, to address delayed cycling, the percent support setting may be decreased or the $E_{SENS}$ setting may be increased (more sensitive). For PS and VS, there is an FAP setting or "rise time %" setting indicating how aggressively the pressure rises. If this setting is too low, then pressure rises sluggishly, which can affect patient support and cycling. This might result in early cycling with the patient continuing to inhale because the pressure rise was not fast enough. In this case, an adjustment could be to increase the "rise time %" setting.

Furthermore, a high lung volume caused by the previous breath with delayed cycling may result in a missed trigger of the subsequent inspiratory effort in patients with Chronic Obstructive Pulmonary Disease (COPD) or with high breathing rates. For patients ventilated with pressure support (PS) ventilation, premature cycling may result in double-triggering or auto-triggering.

Most ventilators in the current market allow the user to select an expiratory cycling setting from a specific range provided by the ventilator. Unlike universal settings such as respiratory rate, PEEP, tidal volume, and pressure support, the expiratory cycling settings are unique to each ventilator. Users who are unfamiliar with a specific ventilator outside their daily use may struggle to properly set the expiratory cycling settings. Moreover, patients need different adjustments when their recovery conditions have changed, or their sedation and pain medications are adjusted. But many clinicians do not adjust the settings optimally to support patient effort.

For example, for triggering the start of exhalation in tube compensated (TC), pressure support (PS) or volume support (VS) ventilation (cycling), the exhalation sensitivity ($E_{SENS}$) setting is frequently left at the default value (25%), which can cause asynchrony in some types of patients. For example, with COPD patients, this value can lead to the patient fighting the ventilator trying to exhale. In proportional assist (PA) ventilation, the exhalation sensitivity ($E_{SENS}$) setting is also frequently left at a default value (such as 3.0 Lpm), which can cause asynchrony in some types of patients. Further, in proportional assist (PA) ventilation, if the percent support setting is set too high, the patient can be over-supported leading to the patient forcing the exhalation mid-way through inspiration. Having the ventilator identify this over-support condition could give the ventilator the ability to detect the patient fighting the ventilator to exhale, not just in PA, but in PS, VS or TC as well. The exhalation issues contribute to poor synchrony.

Therefore, there is a need to have a smarter, or more intuitive, expiratory cycling method to reduce expiratory asynchrony and optimize the patient-to-ventilator interactions.

Accordingly, the systems and methods described herein provide improved exhalation cycling systems and methods. For example, the improved exhalation cycling systems and methods monitor a $P_{MUS}$-based metric to detect patient cycling efforts and/or to determine if the set cycling threshold is appropriate for the patient. Based on this monitoring, the ventilator performs one or more actions. The action may include triggering exhalation, adjusting an exhalation threshold setting, adjusting another ventilator setting, providing a notification, and/or providing a recommendation. For example, the $P_{MUS}$-based metric monitoring can be utilized to adjust $E_{SENS}$ for PS, PA, TC, and VS breath types to improve ventilator cycling or the percent support setting for PA breath type to improve ventilator-patient synchrony. The improved exhalation cycling systems and methods, in these aspects, are referred to herein as "cycling systems and methods" or "cycling settings." The cycling setting reduces the occurrence of cycling asynchrony and requires less operator training or knowledge for effective use. While the cycling setting is referred to herein as a cycling setting, it may also be referred to as a cycling mode, supplemental cycling mode, or supplemental mode because the cycling setting is utilized in conjunction with or in addition to any spontaneous mode of ventilation running any suitable breath type (PS, VS, TC, or PA) for a spontaneous mode of ventilation.

In some aspects, the cycling setting improves ventilator synchrony by changing the cycling threshold or recommending a change in cycling threshold based on the monitoring of estimated patient muscle pressure ($P_{MUS}$) or a $P_{MUS}$-based metric. The $P_{MUS}$-based metric may be $P_{MUS}$, may be a processed signal of $P_{MUS}$, or may represent a shape of the $P_{MUS}$ waveform. In other aspects, the cycling setting improves ventilator synchrony by cycling exhalation based on the monitoring of the $P_{MUS}$-based metric. As estimated patient muscle pressure is a strong indicator of a patient's effort to exhale, a patient $P_{MUS}$-based metric can be utilized to detect cycling or intended cycling and/or to determine if the cycling threshold or pattern is appropriate.

For the purposes of this disclosure, a "breath" refers to a single cycle of inspiration and exhalation delivered with the assistance of a ventilator. The term "breath type" refers to some specific definition or set of rules dictating how the pressure and flow of respiratory gas is controlled by the ventilator during a breath.

A ventilation "mode", on the other hand, is a set of rules controlling how multiple subsequent breaths should be delivered. Modes may be mandatory, that is controlled by the ventilator, or spontaneous, that is that allow a breath to be delivered or controlled upon detection of a patient's effort to inhale, exhale or both. For example, a simple mandatory mode of ventilation is to deliver one breath of a specified mandatory breath type at a clinician-selected respiratory rate (e.g., one breath every 6 seconds). Until the mode is changed, ventilators will continue to provide breaths of the specified breath type as dictated by the rules defining the mode. For example, breath types may be mandatory mode breath types (that is, the initiation and termination of the breath is made by the ventilator) or spontaneous mode breath types (which refers to breath types in which the breath is initiated and/or terminated by the patient). Examples of breath types utilized in the spontaneous mode of ventilation include proportional assist (PA) breath type (including different versions of PA, such as plus and optimized), tube compensated (TC) breath type, volume support (VS) breath type, pressure support (PS) breath type, and etc. Examples of mandatory breath types include a volume control breath type, a pressure control breath type, and etc.

FIG. 1 illustrates a schematic diagram of an aspect of an exemplary ventilator 100. The exemplary ventilator 100 illustrated in FIG. 1 is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb aspect, a fitting, typically referred to as a "wye-fitting" 170, may be provided to couple the patient interface 180 (shown as an endotracheal tube in FIG. 1) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106, accumulator and/or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory valve for controlling gas delivery to the patient 150 and/or gas delivery through the inspiratory limb 132. In some aspects, inspiratory module 104 is configured to provide ventilation according to various ventilator modes, such as mandatory, spontaneous, and/or assist modes.

The expiratory module 108 is configured to release gases from the patient's lungs according to prescribed ventilatory settings. The expiratory module 108 is associated with and/or controls an expiratory valve for releasing gases from the patient 150. In some aspects, expiratory module 108 is configured to release gas according to various ventilator modes, such as mandatory, spontaneous, and/or assist modes.

The ventilator 100 may also include one or more sensors 107 communicatively coupled to ventilator 100. The sensors 107 may be located in the pneumatic system 102, ventilation tubing system 130, and/or on the patient 150. FIG. 1 illustrates a sensor 107 (e.g., flow sensor, pressure sensor, etc.) in pneumatic system 102.

The ventilator 100 may also include one or more non-invasive sensors 107 communicatively coupled to ventilator 100. Sensors are referred to herein as non-invasive when the sensors are located externally to patient. For example, sensors located in the patient wye 170, in the expiratory module 108, in the inspiratory module 104, or on the patient's finger are all external to the patient and are non-invasive. Sensors are referred to herein as invasive when the sensors are located within the patient or placed inside the patient's body, such as sensors located in an endotracheal tube, near a patient diaphragm, or on an esophageal balloon. While invasive sensors can provide great patient data or measurements, these sensors can often be hard to maintain or keep properly positioned. For example, an esophageal balloon can easily be knocked out of proper position in response to patient movement. Once moved, all of the data recorded from the sensors on the balloon are inaccurate. Further, if condensation or material corrupts the sensor and interferes with accurate measurements, the invasive sensor has to be removed from the body to service and/or clean it. Further, because invasive sensors are located within the patient, they usually require the patient to be sedated or undergo a surgical procedure for implantation or positioning adjustment. As such, invasive sensors are burdensome to the patient, hard to implant, hard to maintain, and hard to keep positioned when compared to non-invasive sensors. The embodiment of FIG. 1 illustrates a sensor 107 in pneumatic system 102.

Sensors 107 may communicate with various components of ventilator 100, e.g., pneumatic system 102, other sensors 107, expiratory module 108, inspiratory module 104, processor 116, controller 110, cycling module 118, and any other suitable components and/or modules. A module as used herein refers to memory, one or more processors, storage, and/or other components of the type commonly found in command and control computing devices. In one aspect, sensors 107 generate output, such as measurements, and send this output to pneumatic system 102, other sensors 107, expiratory module 108, inspiratory module 104, processor 116, controller 110, cycling module 118, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or expiratory triggering, for example. Sensors 107 may be placed in any suitable location, e.g., within the ventilatory circuitry or other devices communicatively coupled to the ventilator 100. For example, in some aspects, one or more sensors 107 may be located in an accumulator. Further, sensors 107 may be placed in any suitable internal location, such as, within the ventilatory circuitry or within components or modules of ventilator 100. For example, sensors 107 may be coupled to the inspiratory module 104 and/or expiratory module 108 for detecting changes in, for example, circuit pressure and/or flow. In other examples, sensors 107 may be affixed to the ventilatory tubing or may be embedded in the tubing itself. According to some aspects, sensors 107 may be provided at or near the lungs (or diaphragm) for detecting a pressure in the lungs. Additionally or alternatively, sensors 107 may be affixed or embedded in or near wye-fitting 170 and/or patient interface 180. Any sensory device useful for monitoring changes in measurable parameters during ventilatory treatment may be employed in accordance with aspects described herein. For example, in some aspects, the one or more sensors 107 of the ventilator 100 include an inspiratory flow sensor and an expiratory flow sensor.

As should be appreciated, with reference to the Equation of Motion, ventilatory parameters are highly interrelated and, according to aspects, may be either directly or indirectly monitored. That is, parameters may be directly monitored by one or more sensors 107, as described above, or may be indirectly monitored or estimated by derivation according to the Equation of Motion or other known relationships from the monitored parameters.

The cycling module 118 monitors a physiological parameter of the patient for each sample period from sensor output from one or more sensors. In some aspects, the sample period as used herein refers to a discrete period of time required to monitor a physiological parameter. In some aspects, the sample period is a computation cycle for the ventilator 100. In some aspects, the sample period is every 5 milliseconds (ms), 10 ms, 15 ms, 20 ms, 25 ms, or 30 ms. This list is exemplary only and is not meant to be limiting. Any suitable sample period for monitoring a physiological parameter of the patient may be utilized by the ventilator 100 as would be understood by a person of skill in the art. In some aspects, the cycling module 118 estimates and/or calculates the physiological parameter for monitoring based on the sensor output from one or more sensors. In other aspects, cycling module 118 determines the physiological parameter for monitoring directly from the sensor output received from the one or more sensors. The physiological parameter may be any suitable physiological parameter for determining a patient initiated cycle as would be known by a person of skill in the art. In some aspects, the physiological parameter is flow rate, net flow, pressure, estimated pressure, estimated flow, other derived signals, and/or etc. This list is exemplary only and is not meant to be limiting.

After determining the physiological parameter, the cycling module 118 may send the physiological parameter to any suitable component and/or module of the ventilator 100, such as the pneumatic system 102, expiratory module 108, inspiratory module 104, processor 116, controller 110, and/or etc. In other aspects, the cycling module 118 receives the physiological parameter measurements from other components of the ventilator, such as a sensor 107, controller 110, and/or processor 116.

The cycling module 118 processes the physiological parameter to detect patient cycling efforts. In some aspects, the cycling module 118 processes the physiological parameter to determine a $P_{MUS}$ to detect patient cycling efforts. In further aspects, the cycling module 118 processes the physiological parameter to determine a $P_{MUS}$-based metric to detect patient cycling efforts.

The cycling module 118 calculates the $P_{MUS}$ based on measured flow and/or pressure and based on calculated resistance and/or compliance. During a PA breath type, the ventilator is configured to calculate resistance, compliance, and a $P_{MUS}$ utilizing non-invasive sensor measurements. Unlike other spontaneous breath types, the PA breath type can calculate compliance and resistance. Knowing compliance and resistance, an estimate of the diaphragmatic muscle pressure can be computed non-invasively. In other spontaneous breath types, an invasive sensor located in an esophageal balloon is needed to measure the diaphragmatic pressure. However, an esophageal balloon can easily become dislodged if the patient moves affecting sensor accuracy, is highly invasive to implant, and/or is uncomfortable for a spontaneously breathing patient. Due to the disruptive nature of the esophageal balloon, the esophageal balloon is rarely utilized during a spontaneous breath type. As such, other spontaneous breath types, such as TC, PS and VS, the ventilator is not configured to calculate resistance, compliance, and/or $P_{MUS}$ utilizing non-invasive sensor measurements. Accordingly, the cycling module 118 during a spontaneous breath type that is not a PA breath type will temporarily switch from the current breath type into the PA breath type for a predetermined number of breaths, time or measurements in order to calculate resistance and/or compliance and then estimate $P_{MUS}$ based on one or more non-invasive sensor measurements.

A PA breath type refers to a type of ventilation in which the ventilator acts as an inspiratory amplifier that provides pressure support based on the patient's effort. Usually, the degree of amplification (the "percent support setting") during a PA breath type is set by an operator or clinician, for example as a percentage based on the patient's effort. However, during a temporary implementation of the PA breath type, the cycling module 118 determines the percent support setting provided during the temporary PA breath type.

In one implementation of a PA breath type, the ventilator may continuously monitor the patient's instantaneous inspiratory flow and instantaneous net lung volume, which are indicators of the patient's inspiratory effort. These signals, together with ongoing estimates of the patient's lung compliance and lung/airway resistance and the Equation of Motion $$\left(Pmus = Pwye - \text{Pend\_exp} - (Rtube + Rrs) \times Q_{lung} - \frac{\int Q_{lung} dt}{Crs}\right),$$

allow the ventilator to estimate/calculate a patient effort and derive therefrom a target airway pressure to provide the support that assists the patient's inspiratory muscles to the degree selected by the operator as the percent support setting. In this equation, the patient effort is estimated inspiratory muscle pressure and is negative.

Due to the unique configuration of the PA breath type, the PA breath type is capable of determining a patient respiratory system compliance and/or resistance in an end inspiratory hold of 300 ms or 0.3 seconds, which will usually go unnoticed by a spontaneously breathing patient. In a typical PA breath type, this 300 ms end inspiratory hold is provided intermittently at random. During a temporary PA breath type, the 300 ms end inspiratory hold may be provided in the first, second, third, and/or fourth breath of the temporary PA breath type. Any additional 300 ms holds are provided after a predetermined number of breaths or after a set time period during the temporary PA breath type. In other words, the temporary PA breath type does not provide the 300 ms end inspiratory hold at random but instead at predetermined intervals. As such, the cycling module 118 is able to calculate patient respiratory compliance and patient respiratory system resistance. The cycling module 118 utilizes the following equation to determine patient respiratory system compliance:

$$C_{RAW} = (V_{LUNG}/\text{Pressure\_delta}).$$

The cycling module 118 utilizes the following equation to determine patient respiratory system resistance:

$$R_{RAW} = R_{RAW+ET} - R_{ET},$$

where:

$R_{RAW}$ is patient respiratory system resistance;

$R_{RAW+ET}$ is the combined resistance of the patient respiratory system and the endotracheal tube/tracheostomy tube resistance; and $R_{ET}$ is endotracheal tube/tracheostomy tube resistance.

$R_{RAW+ET}$ is the difference in lung pressure and wye pressure divided by the estimated lung flow. The lung pressure may be based upon the lung pressure at the beginning of exhalation minus exhaled volume times the elastance. Wye pressure is estimated as the measured pressure within the ventilator breathing system (VBS) at the circuit wye, which is compensated for breathing circuit limb resistance.

During the temporary PA breath type, the cycling module 118 calculates patient respiratory resistance and/or compliance based on non-invasive sensor output. The cycling module 118 provides the temporary PA breath type for at least one breath. In some aspects, the cycling module 118 provides the temporary PA breath type for at least three breaths. In some aspects, the cycling module 118 provides the temporary PA breath type until a predetermined number of patient respiratory compliance and/or resistance measurements or calculations have been made by the ventilator 100. In some aspects, the cycling module 118 provides the temporary PA breath type until at least two or three patient respiratory compliance and/or resistance measurements have been made by the ventilator 100. In other aspects, the cycling module 118 provides the temporary PA breath type until at least one, two, three, four, or five patient respiratory compliance and/or resistance measurements have been made by the ventilator 100. The predetermined number of patient respiratory compliance and/or resistance measurements can be completed in 1 breath, 2 breaths, 3 breaths, 5 breaths, 7 breaths, 8 breaths, 10 breaths, 12 breaths, 15 breaths, 20 breaths, 25 breaths or 30 breaths. In other aspects, a predetermined number of patient respiratory compliance and/or resistance measurements can be completed by the cycling module 118 in 4 to 12 breaths.

After the temporary PA breath type has been completed (e.g., the predetermined number of patient respiratory compliance and/or resistance measurements have been made by the ventilator 100), the cycling module 118 switches the ventilation of the patient back to the previously utilized spontaneous breath type (TC, PS or VS).

After the return to the previously utilized spontaneous breath type, the cycling module 118 monitors respiratory data of the patient, such as the non-invasive sensor output. In some aspects, the cycling module 118 calculates a $P_{MUS}$ of the patient during the spontaneous breath type utilizing the respiratory system compliance and/or the respiratory system resistance calculated during the temporary PA breath type, and the current respiratory data measured after the return to TC, VS or PS breath type.

The cycling module 118 measures the $P_{MUS}$ repeatedly throughout a breath. In some aspects, the cycling module 118 measures $P_{MUS}$ every servo cycle, such as every 2 milliseconds, 5 millisecond, or 10 milliseconds. The servo cycle is a fixed, periodic amount of time during which sensor data from sensors 107 are sampled, control calculations are made by the processor 116 or controller 110 of the ventilator 100, and new valve or actuator commands are issued. In some aspects, the sensors 107 send output or measurements every servo cycle. The cycling module 118 communicates the $P_{MUS}$ to other modules, such as the controller 110, the pneumatic system 102, and/or the display 122.

During ventilation with a spontaneous breath type other than the PA breath type, when the $P_{MUS}$-based metric is utilized to determine cycling, the cycling module 118 determines when to perform the temporary switch into the PA breath type by monitoring input to determine the occurrence of one or more conditions. In some aspects, the cycling module 118 monitors the measurements from the non-invasive sensors. In other aspects, the cycling module 118 monitors other received ventilator data or calculations to determine the occurrence of the condition.

In some aspects, the condition may be any event that is indicative of a change in patient respiratory system compliance and/or patient respiratory system resistance, such as a predetermined pressure differential, volume differential, a tidal volume differential, a specific flow waveform shape, a specific volume waveform shape, a specific pressure waveform shape, a predetermined change in pressure, a predetermined change in flow, a predetermined change in tidal volume and/or etc. For example, the condition may be a change in non-invasively monitored flow, pressure, and/or of volume of at least 25%. In other aspects, the condition is an expiration of a set period or predetermined number of breaths, since the last temporary PA breath type switch or since the start of the last temporary PA breath type. For example, the condition may be the expiration of 30, 60, 90, or 120 minutes or the occurrence of 400, 300, or 200 breaths since the last temporary switch into the PA breath type or the start of the last temporary PA breath type. In other examples, the cycling module 118 monitors for the following condition to occur: 1) expiration of 1 hour since the last temporary PA breath type; or 2) a 25% change in one of non-invasively measured pressure, flow, or tidal volume during the spontaneous breath type that is not a PA breath type. If the breath type was just initialized, the conditions discussed above may be monitored from the start of ventilation or the start of the breath type instead of since the last temporary switch into the PA breath type or the start of the last temporary PA breath type. If the cycling module 118 detects a condition, the cycling module 118 of the controller 110 determines a percent support setting and sends instructions to the pressure generating system 102 to provide a short temporary switch into a PA breath type utilizing the determined percent support setting.

In some aspects, the cycling module 118 determines a percent support setting for the temporary PA breath by utilizing a predetermined or preset percent support setting. In other aspects, the cycling module 118 determines a percent support setting based on a target setting for the spontaneous breath type that is not the PA breath type. For example, if the target pressure for the PS breath type is 10 cm $H_2O$, then the cycling module 118 will determine a percent supporting setting for the temporary PA breath to achieve approximately the same pressure level. In another example, if the target volume for a VS breath type is 400 ml, then the cycling module 118 will determine a percent support setting for the temporary PA breath to achieve approximately the same volume level. In other aspects, the percent setting is determined by the cycling module 118 based on outputs from the non-invasive sensor. For example, if inspiratory pressure measurement is 9.8 cm $H_2O$ from inspiratory pressure sensor, then the cycling module 118 will determine a percent support setting for the temporary PA breath to achieve approximately the same pressure level. In further aspects, the cycling module 118 may utilize additional ventilator parameters or inputs to the target setting and/or the outputs from the non-invasive sensor to determine a percent support setting for the temporary PA breath, such as mask type, patient circuit diameter, and etc.

The cycling module 118 may compare the $P_{MUS}$-based metric to a cycling threshold to form a comparison. If the $P_{MUS}$-based metric meets the cycling threshold based on the comparison, the cycling module 118 determines that the patient is making an effort to end inhalation and start exhalation. If the $P_{MUS}$-based metric does not meet the cycling threshold based on the comparison, the cycling module 118 determines that the patient is not making an effort to end inhalation and start exhalation. In response to determining that the patient is not making an effort to end inhalation and start exhalation, the cycling module 118 continues to the monitor the $P_{MUS}$-based metric and compare it to the cycling threshold. The cycling threshold may be dynamic and/or dependent on the magnitude of $P_{MUS}$-based metric.

In response to determining that the patient is making an effort to end inhalation and start exhalation, the cycling module 118 performs one or more actions. The one or more actions may include cycling, providing a notification, providing a recommendation, determining cycling synchrony, displaying a detected cycling effort, recommending a parameter change, and/or automatically changing a parameter.

In some aspects, the one or more actions may include sending a command to end inspiration and begin exhalation. In these aspects, the spontaneous breath types may be adjusted to cycle in response meeting a $P_{MUS}$-based metric threshold instead of based on $E_{SENS}$ (such as a percent of peak flow or a set flow value in Lpm) in PS, VS, TC or PA. In these aspects, the ventilator effectively identifies the end of patient inspiratory effort and determines the optimal time to trigger the expiratory phase. Based on this approach, cycling to the expiratory phase will be variable based on patient effort and will not be purely dependent upon exhaled flow. The cycling module 118 minimizes the patient-to-ventilator asynchrony and provides a feature that is easy to use by the clinician since the clinician does not have to set an $E_{SENS}$ as a primary cycling mechanism.

The one or more actions may include determining if exhalation was provided by the breath type within an interval of time of the detected cycling effort. In these aspects, cycling is still controlled by $E_{SENS}$ in PS, VS, TC and PA and can be influenced by the percent support setting in PA and the rise-time setting in PS or VS. As such, the cycling module 118 determines if the detected cycling effort occurred within a predetermined amount of time of the cycling effort delivered by the spontaneous breath type. In some aspects, the interval of time may be about 300 ms. If the detected effort is not within the interval of time from the delivered exhalation, the cycling module 118 determines asynchronous cycling. In response to determining asynchronous cycling, the cycling module 118 may provide a notification (such as a notification of an asynchronous cycling), provide a recommendation (such as a recommendation to adjust $E_{SENS}$ for a VS, PS, TC or PA breath type or percent support setting for PA breath type), automatically adjust a ventilator setting (such as automatically adjust $E_{SENS}$ for a VS, PS, TC or PA breath type or percent support setting for PA breath type).

In other aspects, the one or more actions may include displaying the detected cycling effort. In some aspects, the detected cycling effort may be displayed on a waveform. In other aspects, a prompt may indicate that a cycling effort was detected and/or missed. In further aspects, the one or more actions may include providing, such as displaying, a recommendation to change a percent support setting in PA, an $E_{SENS}$ setting in PS, VS, TC or PA, or a rise-time setting in PS or VS, as discussed above. For example, if the detected cycling effort happened before exhalation was delivered, the cycling module 118 may recommend increasing the $E_{SENS}$ setting or decreasing the percent support setting. If the detected cycling effort happened after exhalation was delivered, the cycling module 118 may recommend decreasing the $E_{SENS}$ setting or increasing the percent support setting. In further aspects, the one or more actions may include automatically changing a percent support setting in PA, an $E_{SENS}$ setting in PS, VS, TC or PA, or a rise-time setting in PS or VS. For example, if the detected cycling effort happened before exhalation was delivered, the cycling module 118 may automatically increase the $E_{SENS}$ setting or decrease the percent support setting. For example, if the detected cycling effort happened after exhalation was delivered, the cycling module 118 may automatically decrease the $E_{SENS}$ setting or increase the percent support setting.

The cycling module 118 ends inspiration by sending instructions and/or a command to a pneumatic system 102, an expiratory module 108, an inspiratory module 104, a processor 116, and/or a controller 110. The instructions and/or commands cause the one or more ventilator components and/or modules to change the delivered flow and/or pressure and to adjust the valves as needed to end inspiration and start exhalation.

The pneumatic system 102 may include a variety of other components, including mixing modules, valves, tubing, accumulators, filters, etc. Controller 110 is operatively coupled with pneumatic system 102, signal measurement and acquisition systems (e.g., sensor(s) 107), and an operator interface 120 that may enable an operator to interact with the ventilator 100 (e.g., change ventilator settings, select operational modes, view monitored parameters, etc.).

In some aspects, the operator interface 120 of the ventilator 100 includes a display 122 communicatively coupled to ventilator 100. Display 122 may provide various input screens, for receiving clinician input, and various display screens, for presenting useful information to the clinician. In aspects, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some aspects, the display 122 illustrates a physiological parameter, a graph or waveform of the physiological parameter, a graph or waveform of $P_{MUS}$, a detected patient cycle effort, an exhalation sensitivity, a cycle type, a recommendation, a notification, and/or any other information known, received, or stored by the ventilator 100.

In some aspects, controller 110 includes memory 112, one or more processors 116, storage 114, and/or other components of the type commonly found in command and control computing devices. Controller 110 may further include the cycling module 118 as illustrated in FIG. 1. In alternative aspects, the cycling module 118 is located in other components of the ventilator 100, such as in the pressure generating system 102 (also known as the pneumatic system 102) or inspiratory module 104.

The memory 112 includes non-transitory, computer-readable storage media that stores and/or encodes software (or computer readable instructions) that is executed by the processor 116 and which controls the operation of the ventilator 100. In an aspect, the memory 112 includes one or more solid-state storage devices such as flash memory chips. In an alternative aspect, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Figure 2:
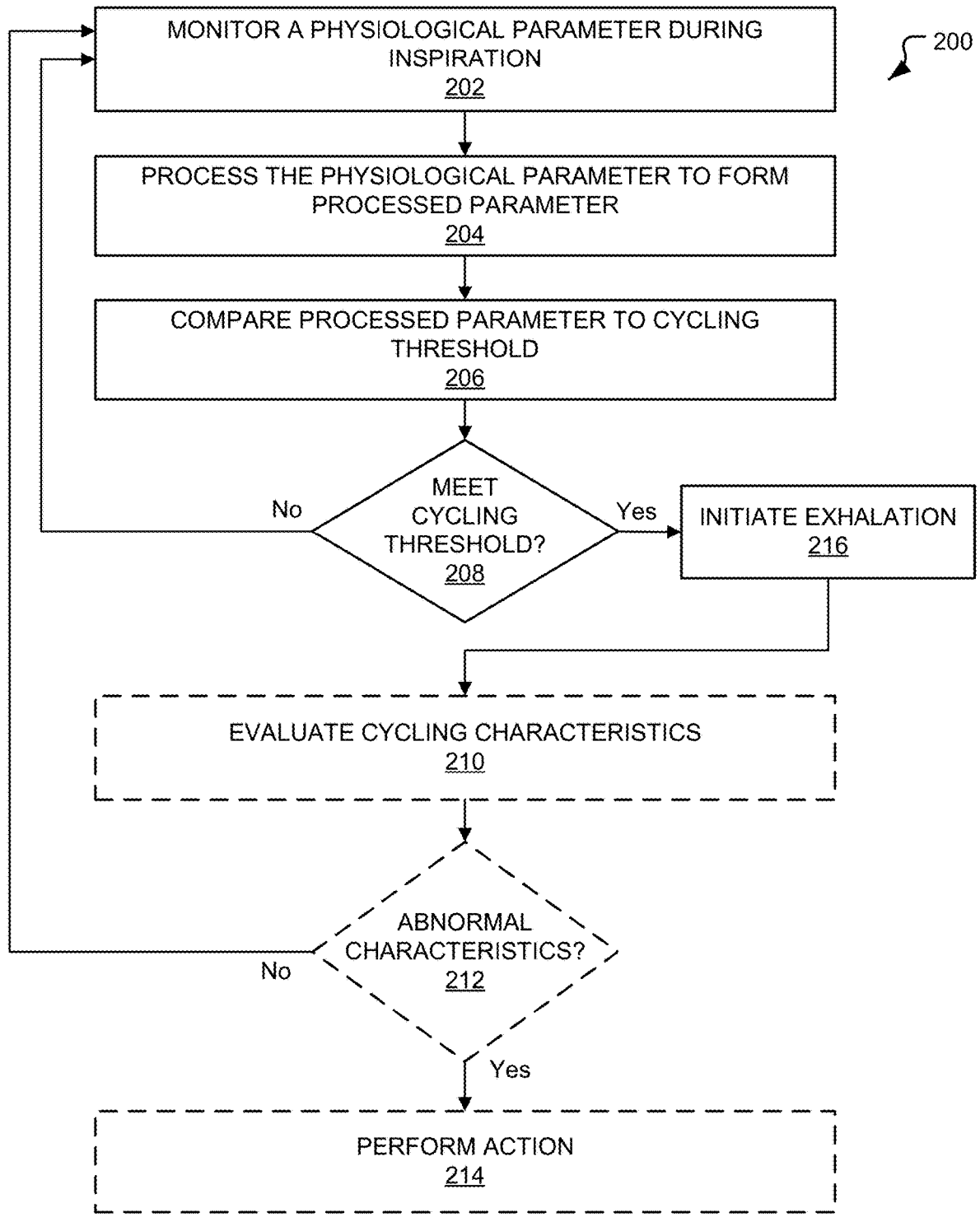
FIG. 2 is a flow diagram illustrating a method for cycling detection based on estimated muscle pressure in a spontaneous breath type during ventilation of a patient with a ventilator, in accordance with aspects of the disclosure.

FIG. 2 illustrates an example of a method 200 for cycling from inspiration to exhalation during ventilation of a patient on a ventilator. In some aspects, method 200 cycles to exhalation based on the monitoring of a $P_{MUS}$-based metric. As such, method 200 provides spontaneous ventilation utilizing a cycling setting. Method 200 begins at the start of spontaneous ventilation utilizing a cycling setting. As discussed above, method 200 can detect a patient's attempt to exhale. In other aspects, method 200 improves ventilator synchrony by detecting patient efforts to exhale and/or by changing or recommending setting changes to improve cycling.

As illustrated, method 200 includes a monitor operation 202, a process operation 204, a compare operation 206, a threshold decision operation 208, and an action operation 214. In some aspects, method 200 also includes an optional timing operation 210 and/or an optional missed cycling determination operation 212.

During the monitor operation 202, the ventilator monitors a physiological parameter based on one or more sensor measurements for each sample period in a first set of sample periods during inspiration. In some aspects, the ventilator during the monitor operation 202 monitors flow, pressure, and/or other derived signals, such as a $P_{MUS}$-based metric. Sensors suitable for this detection may include any suitable sensing device as known by a person of skill in the art for a ventilator, such as an inspiratory flow sensor, inspiratory pressure sensor, an exhalation flow sensor, an exhalation pressure sensor, and/or exhalation auxiliary pressure sensor. In further aspects, the one or more sensor measurements are from one or more non-invasive sensors. In further aspects, the ventilator during the monitor operation 202 is delivering inhalation.

During the process operation 204, the ventilator processes the one or more received sensor measurements of the physiological patient parameter. In some aspects, the ventilator processes the received sensor measurements of the physiological parameter by calculating a $P_{MUS}$ or a $P_{MUS}$- based metric based on the received sensor measurements. Accordingly, the one or more processed parameters include $P_{MUS}$ or a $P_{MUS}$-based metric.

During the compare operation 206, the ventilator compares the one or more processed parameters to a cycling threshold. For example, the $P_{MUS}$-based metric is compared to a cycling threshold. In other aspects, the cycling threshold for the $P_{MUS}$-based metric may be a dynamic function of its magnitude.

Next, during threshold decision operation 208, the ventilator determines if the one or more processed parameters meet a cycling threshold based on the comparison of the one or more processed parameters to the cycling threshold performed during operation 206. In some aspects, the ventilator during threshold decision operation 208 determines a patient intention to cycle based on the comparison of a $P_{MUS}$-based metric to a cycling threshold. For example, the ventilator may determine based on a shape of the $P_{MUS}$ curve a patient intention to cycle. Alternatively, the ventilator may compare one or more measured parameters to an $E_{SENS}$ setting to determine a patient intention to cycle. In other aspects, the ventilator during threshold decision operation 208 determines if a patient intends to cycle based on the comparison of a $P_{MUS}$-based metric to a cycling threshold and scores or grades the asynchrony based on the comparison. An example of a score or grade of asynchrony includes an asynchrony index.

If a patient intention to cycle is detected, the method progresses to cycling operation 216. Additionally, if a patient intention to cycle is detected, an optional evaluation of cycling characteristics may be performed at evaluation operation 210. Alternatively, if a patient intention to cycle is not detected, the method may return to monitor operation 202.

At optional evaluation operation 210, if the ventilator during threshold decision operation 208 determines or detects that a threshold has been met, then the ventilator may evaluate one or more cycling conditions associated with the patient intention to cycle. For instance, the ventilator may evaluate the shape of the $P_{MUS}$ curve. Additionally or alternatively, the ventilator may evaluate a timing of the ventilator cycling versus a timing of the patient intention to cycle. For instance, at evaluation operation 210, the ventilator may evaluate the shape of the $P_{MUS}$ curve to determine whether the curve is normal or abnormal. In other aspects, at evaluation operation 210, the ventilator may evaluate a timing of the detected patient intention to cycle to a timing of the cycling delivered by the ventilator. Based on the evaluation, the ventilator may determine whether characteristics of the patient intention to cycle are normal or abnormal. In aspects, when the $P_{MUS}$ curve is abnormal or the timing of the patient intention to cycle is abnormal, a percent support setting, a rise-time setting, or an $E_{SENS}$ setting may be inappropriate.

At decision operation 212, the ventilator determines or detects if characteristics of the detected patient intention to cycle are normal or abnormal. For instance, if the shape of the Pius curve is indicative of the patient actively exhaling (see e.g., FIG. 5), the Pius curve may be identified as "abnormal." Additionally or alternatively, if the timing of the patient intention to cycle falls outside of a timing threshold, the timing may be identified as "abnormal." In aspects, timing of ventilator cycling may be abnormal when the timing of ventilator cycling is too early (before the patient intention to cycle) or too late (after the patient intention to cycle). In some aspects, the timing of the ventilator cycling may be compared to a patient neural inspiratory time (e.g., a $P_{MUS}$-based characteristic) to determine whether characteristics of the patient intention to cycle are abnormal. If the ventilator determines or detects during decision operation 212 that the characteristics of the patient intention to cycle (e.g., the $P_{MUS}$ curve, the timing, or the like) are not abnormal, the ventilator may return to monitor operation 202. If the ventilator determines or detects during decision operation 212 that the characteristics of the patient intention to cycle (e.g., the $P_{MUS}$ curve, the timing, or the like) are not abnormal, the ventilator is in synchrony with the patient exhalation demand. Alternatively, if the ventilator determines or detects during decision operation 212 that the characteristics of the patient intention to cycle (e.g., the $P_{MUS}$ curve, the timing, or the like) are abnormal, the ventilator may progress to optional action operation 214. If the ventilator determines or detects during decision operation 212 that the characteristics of the patient intention to cycle (e.g., the $P_{MUS}$ curve, the timing, or the like) are abnormal, the ventilator is not in synchrony with the patient exhalation demand.

At optional action operation 214, the ventilator may performs an action. In some aspects, the action is performed in response to detection that characteristics of a patient intention to cycle are abnormal at decision operation 208. In these aspects, the action may be one or more of: a notification of a missed cycling effort, display of a missed cycling effort, a recommendation to change a ventilator setting (e.g., a percent support setting or an $E_{SENS}$ setting), an automatic change of a ventilator setting, and/or notification of an automatic change of ventilator setting. In some aspects, the ventilator may recommend or automatically change percent support setting or an $E_{SENS}$ setting during a PA, TC, VS or PS breath type. In other aspects, the ventilator may additionally or alternatively recommend or automatically change a rise-time setting during a VS or PS breath type.

Figure 3:
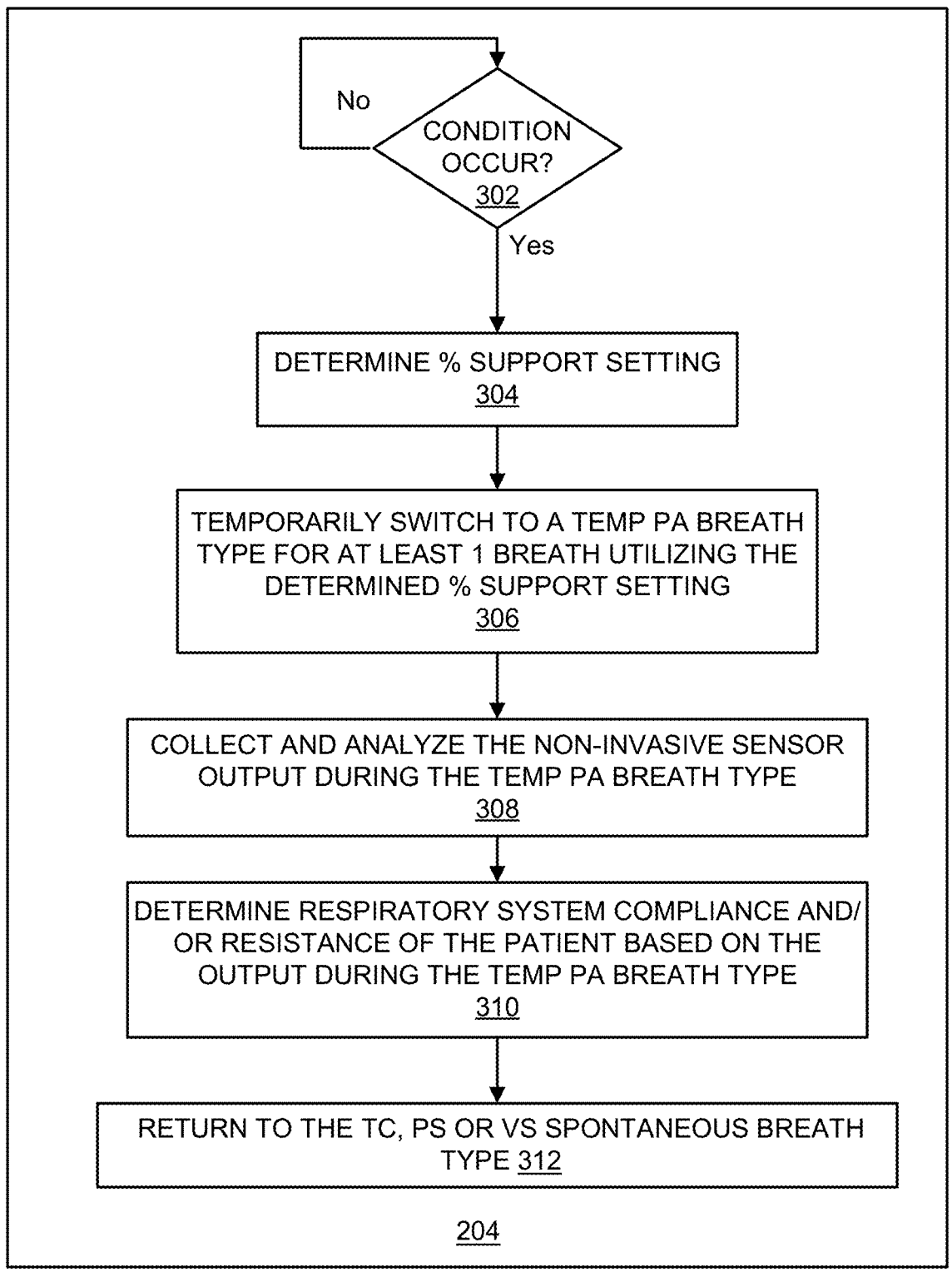
FIG. 3 is a flow diagram illustrating a method for performing process operation 204 of FIG. 2 when the spontaneous breath type is TC, PS or VS and the processed parameter is estimated muscle pressure during ventilation of a patient with a ventilator, in accordance with aspects of the disclosure.

In some aspects, where the processed parameter is a $P_{MUS}$-based metric and the set breath type is TC, PS or VS, the process operation 204 includes several additional steps to determine the $P_{MUS}$-based metric as illustrated in FIG. 3. For example, in these aspects, the process operation 204 may include a determination operation 302, a support setting operation 304, a switch operation 306, an analyze operation 308, a respiratory mechanics estimation operation 310, and a return operation 312.

FIG. 3 is a flow diagram illustrating a method for performing process operation 204 of FIG. 2 when the spontaneous breath type is TC, PS or VS and the processed parameter is a $P_{MUS}$-based metric during ventilation of a patient with a ventilator, in accordance with aspects of the disclosure.

At determination operation 302, the ventilator determines if a condition occurred. In some aspects, the ventilator during determination operation 302 monitors non-invasive sensor output to determine if the condition has occurred. In other aspects, the ventilator during determination operation 302 monitors the number of delivered breaths or the passage of time to determine if a condition has occurred. If the ventilator determines that the condition occurred at determination operation 302, the ventilator selects to perform support setting operation 304. If the ventilator determines that the condition did not occur during determination operation 302, the ventilator selects to continue to monitor the non-invasive sensor output during determination operation 302. The condition may be the expiration of a predetermined amount of time, the delivery of a predetermined number of breaths, and/or a change in one or more monitored parameters that indicates that a change in patient respiratory system compliance and/or resistance has occurred. In some aspects, the condition is a change in monitored pressure, monitored tidal volume, or monitored flow of at least 25%. In other aspects, the condition is expiration of 1 hour from the last use of a temporary PA breath type without a change in monitored pressure, monitored tidal volume, monitored flow by a specific value (such as 3 Lpm), or monitored flow of at least 25% since the last temporary PA breath type. In further aspects, the condition is the delivery of 200 breaths from the last use of the temporary PA breath type without a change in monitored pressure, monitored tidal volume, monitored flow by a specific value (such as 3 Lpm), or monitored flow of at least 25% since the last temporary PA breath type.

At support setting operation 304 the ventilator determines a percent support setting for a temporary PA breath type. In some aspects, at support setting operation 304, the ventilator utilizes a predetermined support setting. In other aspects, at support setting operation 304 the ventilator selects a support setting based on at least one of a target setting from the spontaneous TC, PS or VS breath type or the non-invasively measured respiratory data collected during the TC, PS or VS spontaneous breath type. In further aspects, the ventilator during support setting operation 304 determines other settings for the temporary PA breath type. For example, a PEEP level for the temporary PA breath type may be set based on a PEEP level utilized in the spontaneous TC, PS or VS breath type.

Next, switch operation 306 is performed by the ventilator. At switch operation 306 the ventilator automatically and temporarily switches from the TC, PS or VS spontaneous breath type into a temporary PA breath type for at least one breath utilizing the determined or calculated percent support setting. In some aspects, at switch operation 306 the ventilator automatically and temporarily switches from the spontaneous TC, PS or VS breath type into the temporary PA breath type for at least three breaths utilizing the determined or calculated percent support setting. The temporary PA breath type is performed for at least one breath, at least two breaths, or at least three breaths. In some aspects, the temporary PA breath type is delivered by the ventilator during switch operation 306 until at least one patient respiratory system compliance and/or resistance measurement has been obtained. In some aspects, the temporary PA breath type is delivered by the ventilator during switch operation 306 until at least two different patient respiratory system compliance and/or resistance measurements have been obtained. In some aspects, the temporary PA breath type is delivered by the ventilator during the switch operation 306 until 5, 4, 3, or 2 patient respiratory system compliance and/or resistance measurements have been obtained. As such, the ventilator may deliver ventilation utilizing the temporary PA breath type for at most 4 breaths, 8 breaths, 10 breaths, 12 breaths, 15 breaths, 20 breaths, 30 breaths, 40 breaths, or 50 breaths.

The ventilator during the PA collect and analyze operation 308, collects and analyzes the non-invasively measured respiratory data during the temporary PA breath type. Next, a respiratory mechanics estimation operation 310 is performed by the ventilator. During the respiratory mechanics estimation operation 310, the ventilator calculates or estimates the patient respiratory system compliance and/or resistance based on the non-invasively measured respiratory data taken during the temporary PA breath type during the PA collect and analyze operation 308. If multiple patient respiratory system compliance and/or resistance measurements are taken by the ventilator during respiratory mechanics estimation operation 310, the ventilator determines a compliance measurement and/or a resistance measurement based on these multiple measurements. For example, if multiple patient respiratory system compliance measurements are taken, the ventilator may average the measurements or select the middle or last obtained measurement to be utilized as the temporary PA breath type calculated compliance measurement for use during process operation 204.

At return operation 312 the ventilator switches from the temporary PA breath type back to the previously utilized spontaneous TC, PS or VS breath type. As discussed above, the ventilator returns to the spontaneous TC, VS or PS breath type after a predetermined number of patient respiratory system compliance or resistance measurements have been obtained during the temporary PA breath type, after a predetermined number of breaths, or after a predetermined amount of time.

Figure 4:
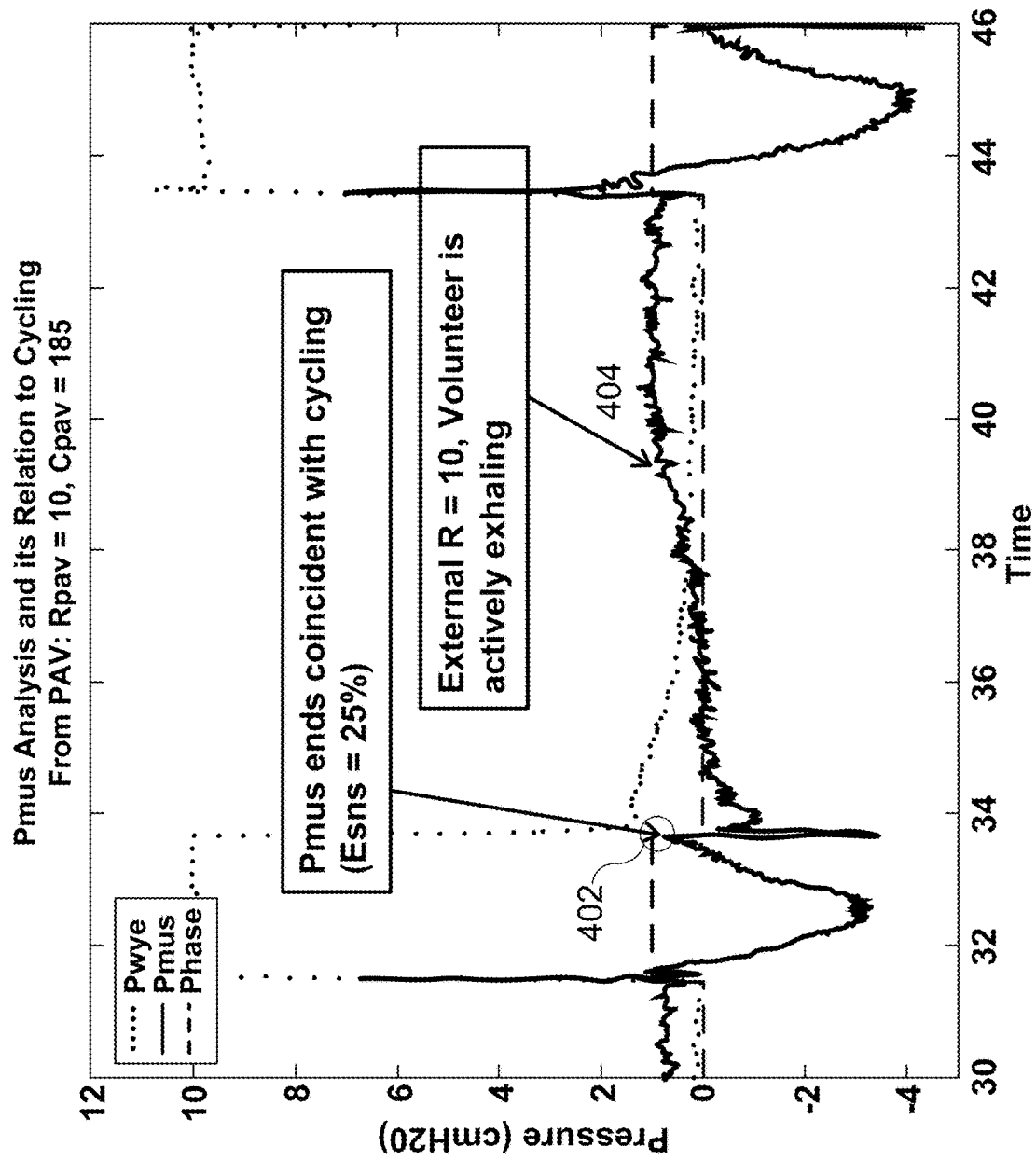
FIG. 4 is a graph illustrating a muscle pressure curve of a volunteer in synchrony with the ventilator and actively exhaling in response to externally imposed breathing resistance.

FIG. 4 is a graph illustrating a $P_{MUS}$ curve of a volunteer in response to additional externally applied resistance. In this example, $P_{MUS}$ ends coincident with cycling at 402 as indicated by the synchronicity with the ventilator phase signal. Upon application of external resistance of 10 (R=10), $P_{MUS}$ of the volunteer is elevated during exhalation, as shown by the upward slope of the $P_{MUS}$ curve at 404. In this case, active exhalation is indicated.

Figure 5:
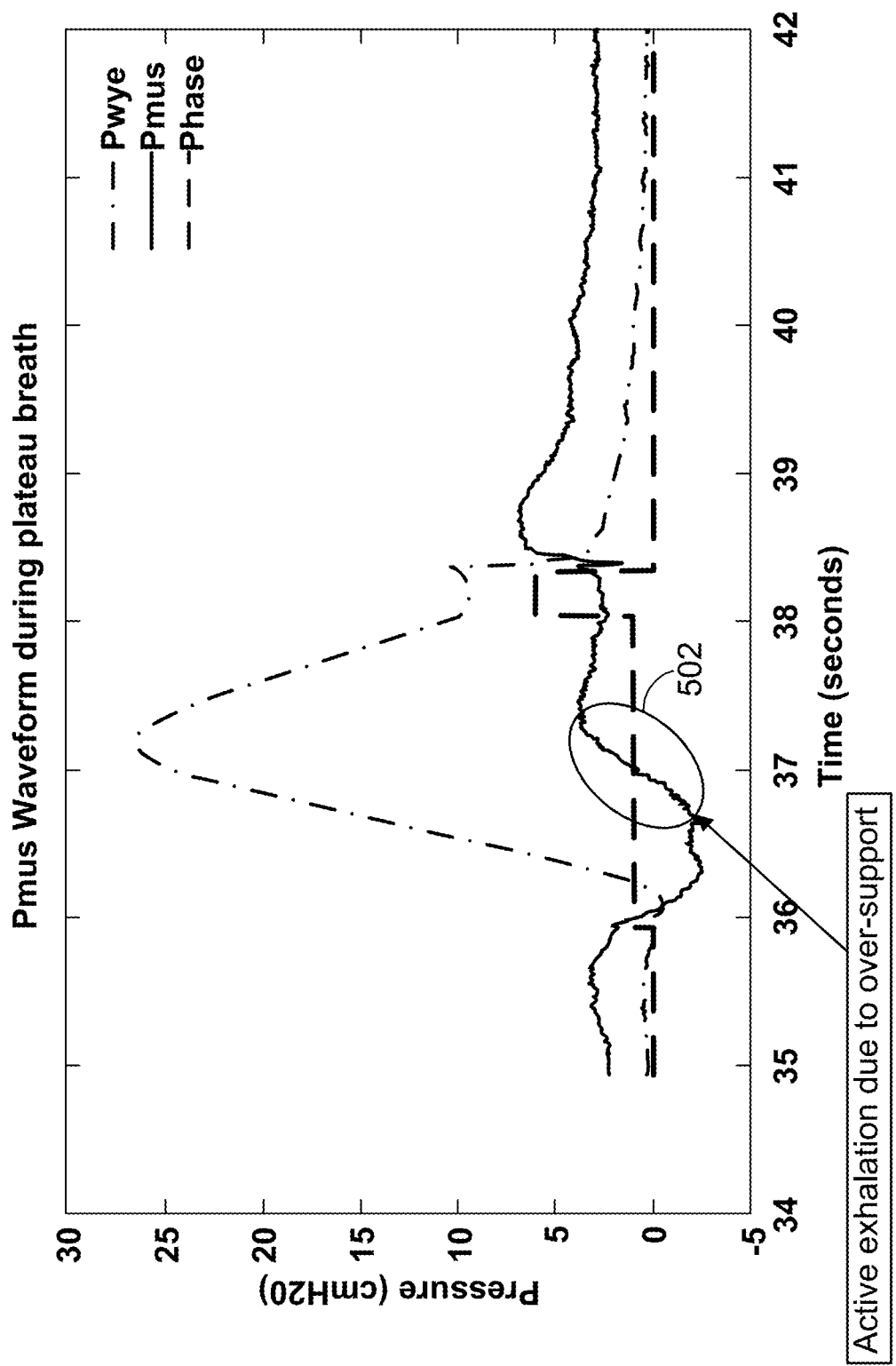
FIG. 5 is a graph illustrating a missed cycle based on estimated muscle pressure monitoring during a high-percentage support using a proportional assist (PA) breath type of a volunteer, in accordance with aspects of the disclosure.

FIG. 5 is a graph illustrating a missed cycle during ventilation of a volunteer in the laboratory with a ventilator based on $P_{MUS}$ monitoring, in accordance with aspects of the disclosure. In this example, the volunteer is being ventilated in a PA breath type with a plateau breath. The PA support setting was set to 95% to force the over-support condition and the volunteer was ventilated. In this case, the volunteer was intentionally over-supported. As shown by FIG. 5, the $P_{MUS}$ shape pushed to positive pressure (as shown by reference circle 502), which indicates that the patient was actively exhaling in response to the over-support. The ventilator did not deliver exhalation until about a 1.5 seconds later, which is outside of a time interval of 300 ms. As such, in this example, the ventilator detects a missed exhalation attempt. Accordingly, the ventilator may perform an action in response to this determination, such as display a missed cycle, indicate that the percent support setting is set too high, recommend lowering the percent support setting, and/or automatically lower the percent support setting to eliminate over-support. Additionally or alternatively, the ventilator indicate that the $E_{SENS}$ setting is too low, may recommend increasing the $E_{SENS}$ setting, or may automatically increase the $E_{SENS}$ setting to improve cycling synchrony.

Figure 6:
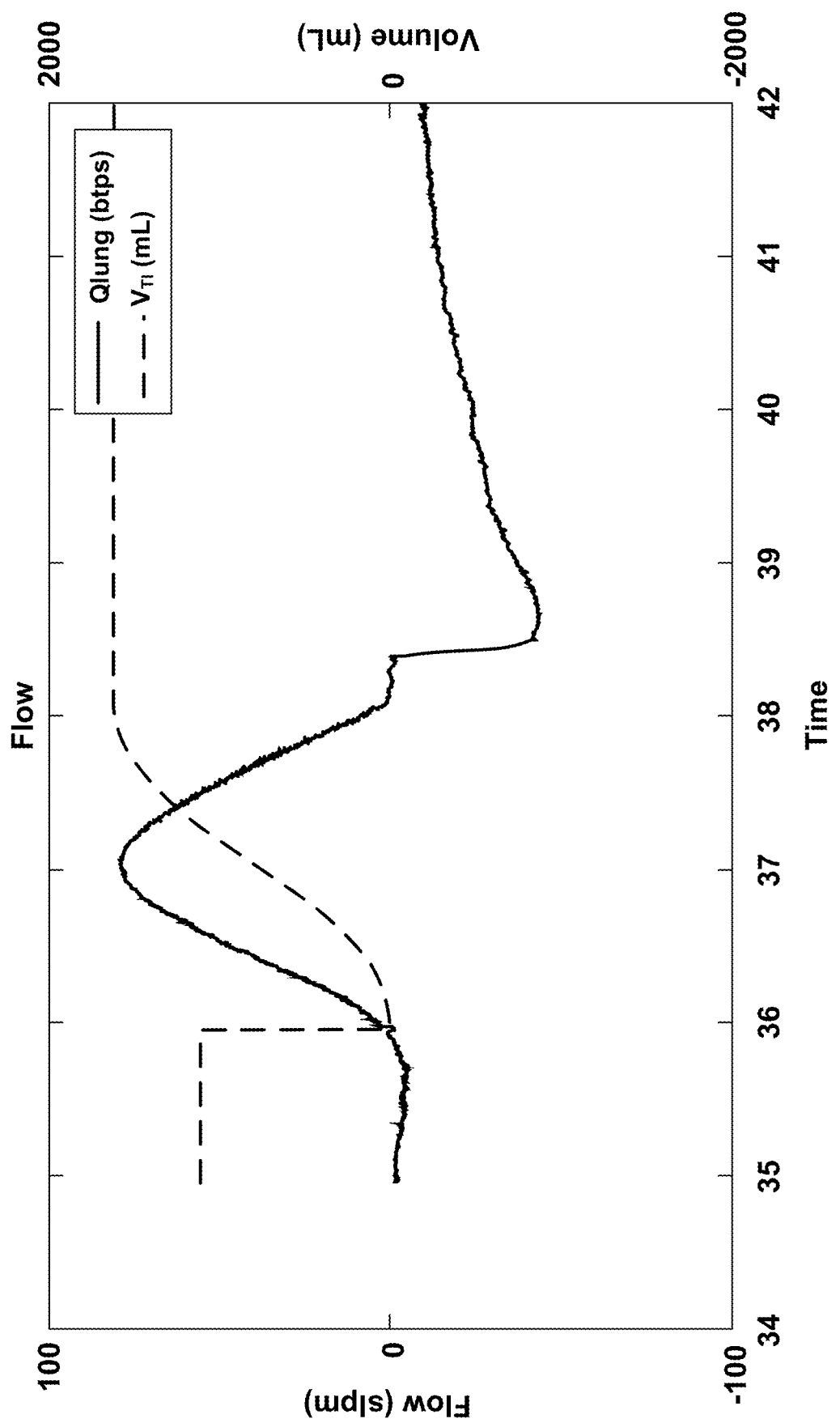
FIG. 6 illustrates the tidal volume and flow curves for ventilation of the volunteer in FIG. 5.

FIG. 6 illustrates the tidal volume and flow curves for ventilation of the volunteer in FIG. 5. At just after time of 37 s, the flow waveform peaks in response to the volunteer pushing back against the ventilator's over-support, that is, actively exhaling to avoid over-delivery. This peak is in synchrony with the pressure waveform peak of FIG. 5. The volume waveform shows the high inspired volume (nearly 1800 mL) in response to this self-truncated breath.

Figure 7:
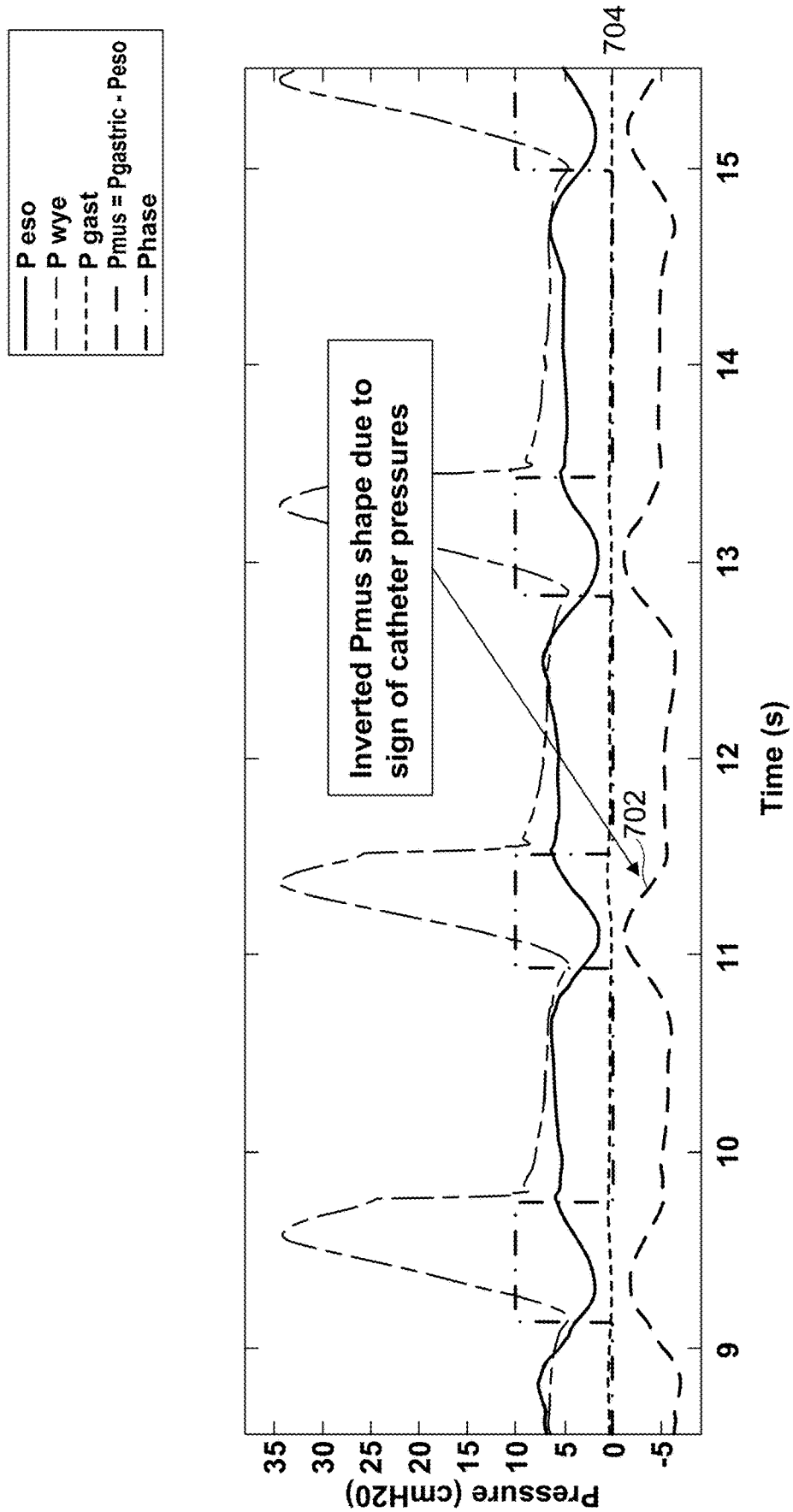
FIG. 7 is a graph illustrating $P_{MUS}$ of an intubated volunteer as measured by an esophageal catheter during a proportional assist (PA) breath type.

FIG. 7 is a graph illustrating $P_{MUS}$ of an intubated volunteer as measured by an esophageal catheter during a PA breath type. In this example, the inverted $P_{MUS}$ shape 702 is due to the sign of the catheter pressures. This waveform shows the relationship between the ventilator pressure at the patient connection port or "wye" and the measured $P_{MUS}$ curve or the difference between the gastric and esophageal pressures that cross the diaphragm muscle (lower large dashed line). In this case, there is late ventilator triggering that might have been created by a trigger sensitivity that was too high. However, the cycling was reasonably synchronous with the end of the $P_{MUS}$ effort. This demonstrates good cycling synchrony.

Figure 8:
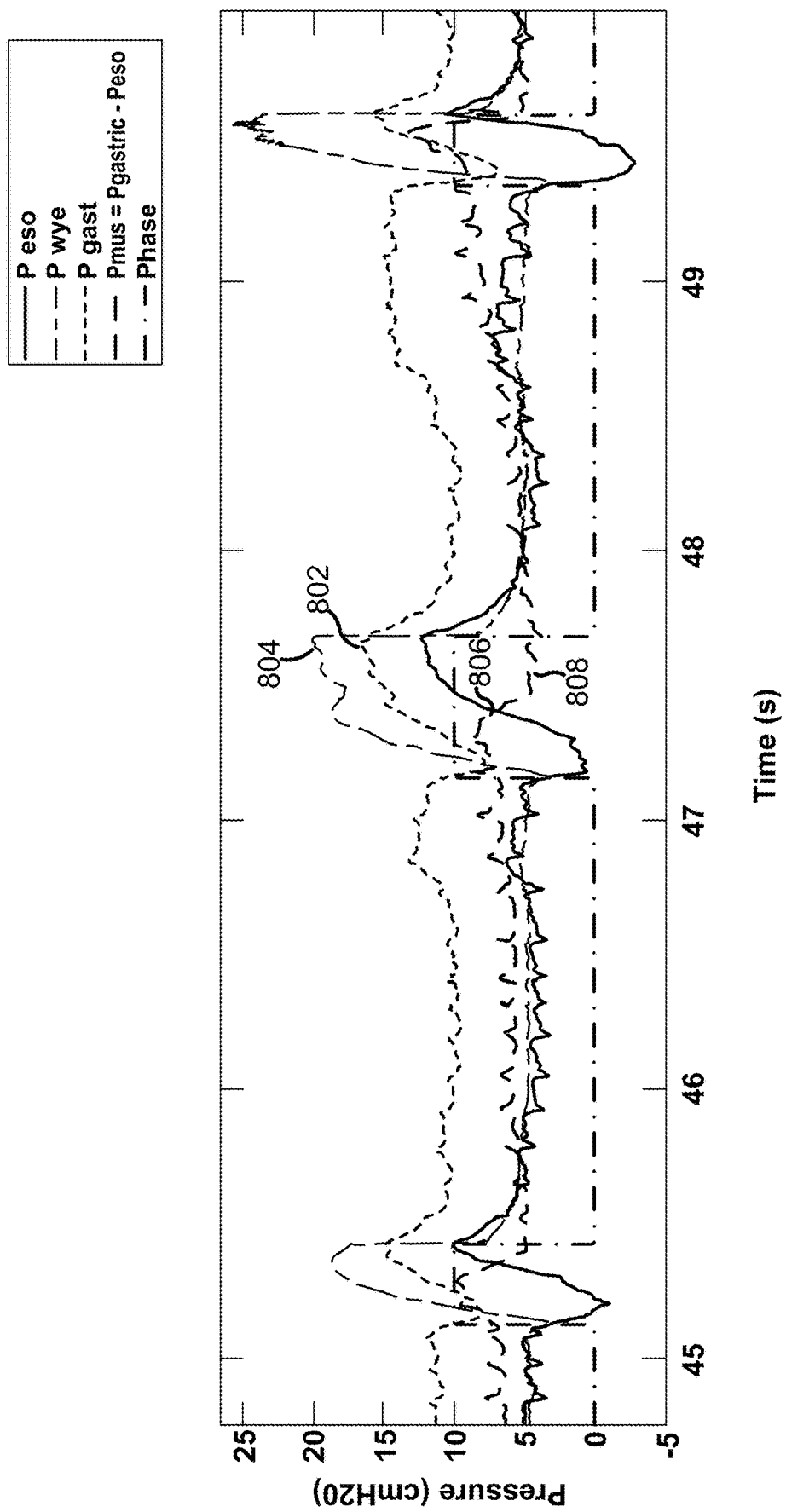
FIG. 8 is a graph illustrating $P_{MUS}$ of an intubated volunteer as measured by a catheter during a high-percentage support, proportional assist (PA) breath type.

FIG. 8 is a graph illustrating $P_{MUS}$ of an intubated volunteer as measured by an esophageal catheter during high-percentage support. In this example, percent support is set to 80% and the patient appears to be pushing against the ventilator due to the rise in gastric pressure at 802. For comparison, see the flat gastric curve at 704 in FIG. 7. Additionally, there is a late rise in Pwye at 804 and an early reversal of $P_{MUS}$ at 806 indicating that the volunteer is actively exhaling in the middle of the inspiratory phase. The $P_{MUS}$ curve also shows a flat push 808 at the end of inhalation to a lower pressure than at the start of the inhalation. Based on the indications associated with oversupport illustrated by FIG. 8, the ventilator may indicate that the percent support setting is set too high, may recommend lowering the percent support setting, and/or may automatically lower the percent support setting to eliminate oversupport. Additionally or alternatively, the ventilator indicate that the $E_{SENS}$ setting is too low, may recommend increasing the $E_{SENS}$ setting, or may automatically increase the $E_{SENS}$ setting to improve cycling synchrony.

Those skilled in the art will recognize that the methods and systems of the present disclosure may be implemented in many manners and as such are not to be limited by the foregoing exemplary aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A ventilator system comprising:
at least one sensor;
a gas-delivery system configured to deliver ventilation gases to a patient;
at least one processor; and
at least one memory comprising computer-executable instructions that when executed by the at least one processor cause the ventilator system to:
receive one or more sensor measurements from the at least one sensor during inhalation of the patient;
based on the one or more sensor measurements, estimate a muscle pressure ($P_{MUS}$) of the patient during the inhalation of the patient;
determine a $P_{MUS}$-based metric based on the estimate of $P_{MUS}$;
in response to determining that the $P_{MUS}$-based metric meets a cycling threshold, determine a patient intention to cycle from inhalation to exhalation;
evaluate one or more characteristics of the patient intention to cycle from inhalation to exhalation;
when the one or more characteristics of the patient intention to cycle from inhalation to exhalation are not normal, determining a missed cycling effort; and
perform an action in response to the missed cycling effort.

2. The ventilator system of claim 1, wherein ventilation is delivered to the patient based on one of: a volume support (VS) breath type, a pressure support (PS) breath type, or a tube compensated (TC) breath type.

3. The ventilator system of claim 2, wherein the computer-executable instructions further causing the ventilator system to:
temporarily switch to a proportional assist (PA) breath type; and
while delivering the temporary PA breath type, receive the one or more sensor measurements from the at least one sensor during the inhalation of the patient.

4. The ventilator system of claim 3, wherein the computer-executable instructions further causing the ventilator system to:
estimate a respiratory mechanics parameter based on the one or more sensor measurements; and
based on the estimated respiratory mechanics parameter, estimate the $P_{MUS}$ of the patient during the inhalation of the patient.

5. The ventilator system of claim 2, wherein the computer-executable instructions further causing the ventilator system to:
determine a percent support setting based on one of a pressure support setting or a volume support setting.

6. The ventilator system of claim 5, wherein the computer-executable instructions further causing the ventilator system to:
temporarily switch to a proportional assist (PA) breath type; and
deliver at least one breath based on the determined percent support setting.

7. The ventilator system of claim 4, wherein the computer-executable instructions further causing the ventilator system to:
return to the ventilation delivered to the patient based on one of: the volume support (VS) breath type, the pressure support (PS) breath type, or the tube compensated (TC) breath type.

8. The ventilator system of claim 7, wherein the computer-executable instructions further causing the ventilator system to:
automatically change at least one of a pressure support setting, a volume support setting, or an exhalation sensitivity ($E_{SENS}$) setting while delivering ventilation to the patient according to one of: the volume support (VS) breath type, the pressure support (PS) breath type, or the tube compensated (TC) breath type.

9. The ventilator system of claim 1, wherein the action comprises displaying a notification or automatically adjusting at least one setting.

10. A method of determining a patient intention to cycle, comprising:
    delivering spontaneous ventilation to a patient;
    based on a target setting for the spontaneous ventilation, determining a percent support setting;
    temporarily switching to a proportional assist (PA) breath type;
    delivering at least one PA breath based on the determined percent support setting;
    receiving one or more sensor measurements from at least one sensor during the at least one PA breath;
    based on the one or more sensor measurements, estimating a muscle pressure ($P_{MUS}$) of the patient; and
    in response to determining that the $P_{MUS}$ meets a cycling threshold, determining a patient intention to cycle from an inspiratory phase of a PA breath to an expiratory phase of the PA breath.

11. The method of claim 10, further comprising:
    in response to determining the patient intention to cycle, comparing a timing of the patient intention to cycle to a timing of exhalation delivery by the ventilator; and
    when the timing of the patient intention to cycle exceeds a timing threshold, determining a missed cycling effort.

12. The method of claim 11, further comprising:
    performing an action in response to the missed cycling effort.

13. The method of claim 12, wherein the action comprises at least one of: displaying a notification or automatically adjusting the target setting for the spontaneous ventilation.

14. The method of claim 13, wherein the notification comprises at least one of: displaying an indication of the missed cycling effort or displaying an indication to adjust the target setting.

15. The method of claim 10, wherein the spontaneous ventilation is delivered based on one of: a volume support (VS) breath type, a pressure support (PS) breath type, or a tube compensated (TC) breath type.

16. A method for detecting a patient intention to cycle during spontaneous ventilation of the patient on a ventilator, comprising:
    monitoring at least one parameter of the patient receiving spontaneous ventilation based on one or more received non-invasive sensor measurements during inhalation;
    estimating a muscle pressure ($P_{MUS}$) of the patient during the inhalation based on the one or more received non-invasive sensor measurements;
    comparing a $P_{MUS}$-based metric to a cycling threshold;
    determining that the $P_{MUS}$-based metric meets the cycling threshold to identify a patient intention to cycle from inhalation to exhalation;
    in response to identifying the patient intention to cycle, evaluating one or more characteristics of the patient intention to cycle;
    when the one or more characteristics of the patient intention to cycle are abnormal, determining a missed cycling effort; and
    performing an action in response to the missed cycling effort.

17. The method of claim 16, further comprising:
    temporarily switching to a proportional assist (PA) breath type; and
    while delivering the temporary PA breath type, receiving the one or more sensor measurements from at least one sensor during the inhalation of the patient.

18. The method of claim 17, further comprising:
    estimating a respiratory mechanics parameter based on the one or more sensor measurements; and
    based on the estimated respiratory mechanics parameter, estimating the $P_{MUS}$ of the patient during the inhalation of the patient.

19. The method of claim 18, wherein the estimated respiratory mechanics parameter is at least one of: a resistance or a compliance of the patient.

20. The method of claim 16, wherein the spontaneous ventilation is delivered based on one of: a volume support (VS) breath type, a pressure support (PS) breath type, or a tube compensated (TC) breath type.

* * * * *